US011724083B2

(12) United States Patent
Spataro et al.

(10) Patent No.: US 11,724,083 B2
(45) Date of Patent: Aug. 15, 2023

(54) INSTRUMENT DELIVERY DEVICE HAVING A MULTI-POSITION ROTARY ELEMENT

(71) Applicant: Becton, Dickinson and Company, Franklin Lakes, NJ (US)

(72) Inventors: Joseph Spataro, Cottonwood Heights, UT (US); Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 789 days.

(21) Appl. No.: 16/849,280

(22) Filed: Apr. 15, 2020

(65) Prior Publication Data

US 2020/0330722 A1 Oct. 22, 2020

Related U.S. Application Data

(60) Provisional application No. 62/835,935, filed on Apr. 18, 2019.

(51) Int. Cl.
*A61M 39/10* (2006.01)
*A61B 5/15* (2006.01)
*A61M 25/01* (2006.01)
*A61M 25/00* (2006.01)

(52) U.S. Cl.
CPC ..... *A61M 39/105* (2013.01); *A61B 5/150992* (2013.01); *A61M 25/0113* (2013.01); *A61M 39/1055* (2013.01); *A61M 25/003* (2013.01); *A61M 25/0084* (2013.01); *A61M 2025/0031* (2013.01); *A61M 2025/0089* (2013.01); *A61M 2039/1072* (2013.01)

(58) Field of Classification Search
CPC .... A61B 5/150992; A61M 2025/0004; A61M 2025/0031; A61M 2025/0089; A61M 2025/0175; A61M 2039/0036; A61M 2039/1072; A61M 2039/226; A61M 25/003; A61M 25/0084; A61M 25/0097; A61M 25/0105; A61M 25/0113; A61M 25/02; A61M 25/0606; A61M 25/0612; A61M 39/10; A61M 39/105; A61M 39/1055; A61M 39/22; A61M 39/26
See application file for complete search history.

(56) References Cited

U.S. PATENT DOCUMENTS 6,086,008 A 7/2000 Gray et al.
2008/0319387 A1 12/2008 Amisar et al.

FOREIGN PATENT DOCUMENTS

EP 2386327 11/2011
WO 2014/062013 4/2014
WO 2015/013251 1/2015

*Primary Examiner* — Shefali D Patel
(74) *Attorney, Agent, or Firm* — Kirton McConkie; Whitney Blair; Kevin Stinger

(57) ABSTRACT

A delivery device for delivering an instrument through an intravenous catheter may include a housing, a rotary element disposed within the housing, and the instrument. In some embodiments, the rotary element may include a groove, which may extend around at least a portion of a circumference of the rotary element. In some embodiments, the instrument may be disposed within the groove and/or between the rotary element and the housing. In some embodiments, in response to rotation of the rotary element with respect to the housing, the instrument may be advanced distally through a port of the housing. In some embodiments, the instrument may include a guidewire, a probe, tubing, or a light tube.

20 Claims, 20 Drawing Sheets

INSTRUMENT DELIVERY DEVICE HAVING A MULTI-POSITION ROTARY ELEMENT

RELATED APPLICATION

This application claims the benefit of U.S. Patent Application No. 62/835,935, filed Apr. 18, 2019, and entitled INSTRUMENT DELIVERY DEVICE HAVING A MULTI-POSITION ROTARY ELEMENT, which is incorporated herein in its entirety.

BACKGROUND

Insertion of a needle into vasculature of a patient tends to invoke apprehension in the patient, as well as the clinician, for various reasons. Blood draws are a common source of needle insertions. Attempts have been made to utilize peripheral intravenous catheters (PIVCs) for withdrawing blood from the vasculature of the patient, which may reduce may a number of needle insertions experienced by a given patient.

A common type of IV catheter is an over-the-needle PIVC. As its name implies, the over-the-needle PIVC may be mounted over an introducer needle having a sharp distal tip. The sharp distal tip may be used to pierce skin and the vasculature of the patient. Insertion of the PIVC into the vasculature may follow the piercing of the vasculature by the needle. The needle and the PIVC are generally inserted at a shallow angle through the skin into the vasculature of the patient with a bevel of the needle facing away from the skin of the patient. Once placement of the needle within the vasculature has been confirmed, the clinician may temporarily occlude flow in the vasculature and withdraw the needle, leaving the PIVC in place for future blood withdrawal and/or fluid infusion.

There may be several limitations to the current PIVC blood draw approach. Current use of a PIVC to draw blood can be slow and somewhat inefficient, particularly when the patient has difficult intra-venous access or veins that are not readily accessed by the clinician. Also, blood samples obtained via a PIVC may often need to be discarded due to concerns regarding sample quality. Furthermore, current use of a PIVC to draw blood may result in kinking of tubing. Moreover, the PIVC may narrow, collapse, or clog with time, leading to failure of the PIVC.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to a delivery device and related systems and methods for delivering an instrument through an intravenous catheter. In some embodiments, the instrument may include a guidewire, a probe, tubing, a light tube, or another suitable instrument. In some embodiments, the instrument may include a first end and a second end.

In some embodiments, the delivery device may include a housing, which may include a port. In some embodiments, the delivery device may include a rotary element, which may be disposed within the housing. In some embodiments, the rotary element may include a channel and a groove, which may extend around at least a portion of a circumference of the rotary element. In some embodiments, the delivery device may include the instrument, which may be disposed within the groove and/or between the rotary element and the housing. In some embodiments, in response to rotation of the rotary element with respect to the housing, the instrument may be advanced through the port.

In some embodiments, the delivery device may include a connector, which may be stationary with respect to the housing. In some embodiments, the connector may include a primary fluid pathway and multiple secondary fluid pathways in fluid communication with the primary fluid pathway. In some embodiments, the connector may be fixed to the housing and/or integrally formed with the housing as a single unit. In some embodiments, the connector may include a luer adapter.

In some embodiments, the rotary element may be configured to rotate with respect to the housing between a first position and a second position. In some embodiments, in response to the rotary element being in the first position, the second end of the instrument may be aligned with the secondary fluid pathways, the channel may not be aligned with the secondary fluid pathways, and the first end of the instrument may be disposed in a first location or position. In some embodiments, the second end of the instrument may be aligned with a particular one of the secondary fluid pathways.

In some embodiments, in response to the rotary element being in the second position, the channel may be aligned with the secondary fluid pathways, the second end of the instrument may not be aligned with the secondary fluid pathways, and the first end of the instrument may be disposed in a second location.

In some embodiments, in response to rotation of the rotary element from the second position to the first position, the instrument may be advanced distally through the port. In some embodiments, the rotary element may rotate from the first position to the second position in response to rotation of the rotary element less than a full turn or another amount.

In some embodiments, the rotary element may be configured to rotate with respect to the housing between the first position, the second position, and a third position. In some embodiments, in response to the rotary element being in the third position, the second end of the instrument may be aligned with the secondary fluid pathways, the channel may be aligned with the secondary fluid pathways, and the first end of the instrument may be disposed in a third location.

In some embodiments, in response to rotation of the rotary element from the third position to the first position, the instrument may be advanced distally through the port. In some embodiments, the rotary element may rotate from the first position to the third position in response to rotation of the rotary element about one-fourth of a full turn or another amount.

In some embodiments, the first position may correspond to a blood draw position, configured to collect blood from a patient. In some embodiments, a blood collection device maybe coupled to the connector. In some embodiments, the instrument may include tubing, which may facilitate collection of blood from the patient. In some embodiments, the tubing may include a variable inner diameter and/or a variable outer diameter. In some embodiments, the second position may correspond to an infusion position, configured to infuse fluid into vasculature of the patient. In some embodiments, a fluid infusion device may be coupled to the connector. In some embodiments, the third position may correspond to a flush position, configured to flush the channel and the tubing. Thus, in some embodiments, the delivery device may be configured to provide multiple functions, including blood draw, infusion, and flushing, via a single port.

In some embodiments, a catheter system may include a catheter assembly and the delivery device, which may be coupled to the catheter assembly. In some embodiments, the catheter assembly may include a catheter adapter and/or a catheter, which may extend distally from the catheter adapter. In some embodiments, in response to the rotary element being in the first position, the first end of the instrument may be disposed in the first location, which may be distal to the distal end of the catheter. In some embodiments, in response to the rotary element being in the second position, the first end of the instrument may be disposed in the second location, which may be proximal to the distal end of the catheter. In some embodiments, in response to the rotary element being in the third position, the first end of the instrument may be disposed in the third location, which may be proximal to the distal end of the catheter and/or distal to the second location.

In some embodiments, the catheter system may include an extension tube, which may include a distal end and a proximal end. In some embodiments, the distal end of the extension tube may be coupled to the catheter adapter. In some embodiments, the proximal end of the extension tube may be coupled to the housing of the delivery device. In some embodiments, the proximal end of the extension tube may be integrated within the port of the housing, which may eliminate manual connection of the delivery device to the extension tube. In some embodiments, the distal end of the extension tube may be integrated within a port of the catheter adapter.

In some embodiments, the groove may include a width approximately equal to or slightly greater than the instrument, which may facilitate support of the instrument and/or decrease a risk of kinking of the instrument. In some embodiments, the groove may extend inwardly from the circumference of the rotary element. In some embodiments, the groove may extend inwardly from the circumference of the rotary element to and/or towards a central axis of rotation of the rotary element. In some embodiments, the second end of the instrument may be secured within the delivery device, such as, for example, within the groove.

In some embodiments, the housing may include a first port and a second port. In some embodiments, the housing may include a protrusion. In some embodiments, the rotary element may include an upper end and a lower end. In some embodiments, the upper end may include the connector. In some embodiments, the rotary element may include a lumen, which may extend through the upper end and the lower end. In some embodiments, the rotary element may include an upper septum and/or a lower septum disposed within the lumen.

In some embodiments, in response to connection of a medical device to the connector, the upper septum may be configured to move towards the lower septum to allow fluid to flow around the upper septum. In some embodiments, in response to the rotary element being rotated to the first position: the lower septum may contact the protrusion and be moved towards the opening; the lower septum may divide the lumen into an upper chamber and a lower chamber sealed from the upper chamber; the upper chamber may be in fluid communication with the second end of the instrument; the instrument may extends through the first port; and the first end of the instrument may be disposed in a particular first location. In some embodiments, the second port may be in fluid communication with the lower chamber.

In some embodiments, in response to the rotary element being rotated to the second position, the lower septum may move away from the opening; the upper chamber, the lower chamber, and the second end of the instrument may be in fluid communication; and the first end of the instrument may be disposed in a particular second location. In some embodiments, the lumen may include a spring, which may urge the upper septum upwardly against the housing to prevent fluid from flowing around the upper septum. In some embodiments, the delivery device may include a channel disposed between the lower end of the rotary element and the housing. In some embodiments, the channel may be in fluid communication with the lower chamber.

The object and advantages of the embodiments will be realized and achieved at least by the elements, features, and combinations particularly pointed out in the claims. It is to be understood that both the foregoing general description and the following detailed description are exemplary and explanatory and are not restrictive of the invention, as claimed.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
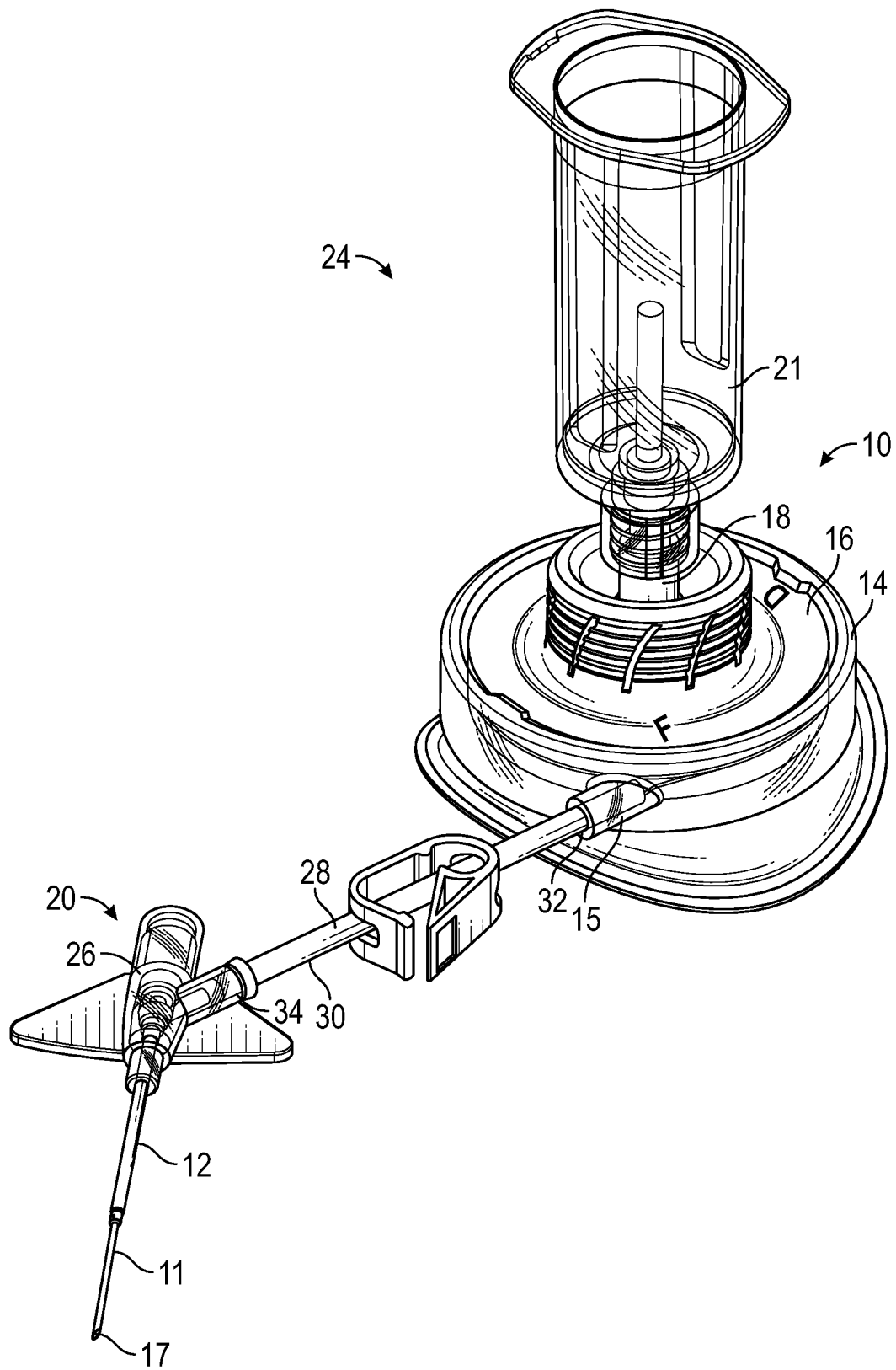
FIG. 1A is an upper perspective view of an example catheter system, according to some embodiments.

As used in the present disclosure, the term "distal" refers to a portion of a catheter system or component thereof that is farther from a user, and the term "proximal" refers to a portion of a catheter system or component thereof that is closer to the user. As used in the present disclosure, the term "user" may refer to a clinician, doctor, nurse, or any other care provider and may include support personnel.

Referring now to FIG. 1, in some embodiments, a delivery device 10 may be configured to deliver an instrument 11 through an intravenous catheter 12. In some embodiments, the intravenous catheter 12 may include a PIVC, a peripherally inserted central catheter (PICC), a midline catheter, or another suitable catheter. In some embodiments, the instrument 11 may include a guidewire, a probe, tubing, a light tube, or another suitable instrument.

In some embodiments, the delivery device 10 may include a housing 14, which may include a port 15. In some embodiments, the delivery device 10 may include a rotary element 16, which may be disposed within the housing 14. In some embodiments, in response to rotation of the rotary element 16 with respect to the housing 14 in a first direction, such as, for example, clockwise, the instrument 11 may be advanced in a distal direction. In some embodiments, a first end 17 of the instrument 11 may be advanced and/or retracted. In some embodiments, in response to rotation of the rotary element 16 with respect to the housing 14 in an opposite direction as the first direction, such as, for example, counterclockwise, the instrument 11 may be retracted in a proximal direction.

In some embodiments, the rotary element 16 may include a connector 18, which may include a luer adapter. In some embodiments, the luer adapter may be coupled to a needleless connector. In some embodiments, the connector 18 may include the needleless connector, which may be directly coupled to the rotary element 16. In some embodiments, a medical device 21 coupled to the connector 18 may not move along an axis of the intravenous catheter 12. In some embodiments, the medical device 21 may be integrated with the connector 18. In some embodiments, the medical device 21 may be monolithically formed with connector 18 as a single unit.

In some embodiments, the medical device 21 may include a blood collection device, an infusion device, or another medical device. In some embodiments, the blood collection device may include a syringe, a vacuum tube, a blood collection tube, a holder (as illustrated, for example, in FIG. 1A), etc. In some embodiments, the holder may include a cannula configured to puncture a seal of a particular blood collection device. In some embodiments, the connector 18 may be coupled to the rotary element 16 and/or integrally formed with the rotary element 16. In some embodiments, the connector 18 may be monolithically formed with rotary element 16 as a single unit. In some embodiments, the medical device 21 may rotate with the rotary element 16.

In some embodiments, the delivery device 10, via rotation of the rotary element 16, may serve multiple purposes, such as, for example, one or more of the following: blood draw, infusion, and flushing. Further, in some embodiments, the delivery device 10 may eliminate a need to connect a brand new delivery device 10 whenever blood draw is desired. In some embodiments, because the delivery device 10 may serve multiple purposes and reduce a need to disconnect and connect devices from a catheter assembly 20, the delivery device 10 may reduce a risk of dislodgement of the intravenous catheter 12 from an insertion site. In some embodiments, a patient may feel a renewed sense of confidence in knowing that the delivery device 10 serves multiple purposes, such as, for example, blood draw, infusion, and flushing.

In some embodiments, the delivery device 10 may reduce priming volume. In some embodiments, the delivery device 10 may facilitate infusion of a medication through the instrument 11 to deliver the medication to a location in the vasculature with accelerated hemo-dilution. In some embodiments, a distal end 22 of the intravenous catheter 12 may include one or more diffusion holes. In these and other embodiments, the medication may be delivered through the instrument 11 while other fluid is delivered to the patient via the diffusion holes (which may be disposed at the distal end 22 of the intravenous catheter 12), which may facilitate dilution of the medication as it is delivered in the vasculature and may reduce a risk of vein damage due to a high concentration of the medication.

In some embodiments, a catheter system 24 may include the catheter assembly 20 and the delivery device 10, which may be coupled to the catheter assembly 20. In some embodiments, the catheter assembly 20 may include a catheter adapter 26 and/or the intravenous catheter 12, which may extend distally from the catheter adapter 26.

In some embodiments, the delivery device 10 may be directly coupled to a proximal end of the catheter adapter 26. In these and other embodiments, the catheter assembly 20 may include a straight or non-integrated catheter assembly. In some embodiments, the catheter assembly 20 may include an integrated catheter assembly. In further detail, in some embodiments, the catheter adapter 26 of the catheter assembly 20 may include an integrated extension tube, such as, for example, the BD NEXIVA™ Closed IV Catheter System, the BD NEXIVA™ DIFFUSICS™ Closed IV Catheter System, or the Becton Dickinson PEGASUS™ Safety Closed IV Catheter System.

In some embodiments, the catheter system 24 may include an extension tube 28, which may include a distal end 30 and a proximal end 32. In some embodiments, the extension tube 28 may be short, which may allow the instrument 11 to be shorter. In some embodiments, the distal end 30 of the extension tube 28 may be coupled to the catheter adapter 26. In some embodiments, the proximal end 32 of the extension tube 28 may be coupled to the housing 14 of the delivery device 10. In some embodiments, the proximal end 32 of the extension tube 28 may be integrated within the port 15 of the housing 14, which may eliminate manual connection of the delivery device to the extension tube. In some embodiments, the distal end 30 of the extension tube 28 may be integrated within a port 34 of the catheter adapter 26. In some embodiments, the delivery device 10 may reduce a number of user-initiated connections, which may reduce stress and a contamination risk for the user. Furthermore, in some embodiments, the user is not limited to a small selection of needleless connectors, nor will the blood draw experience be tied to a specific connector.

Figure 1B:
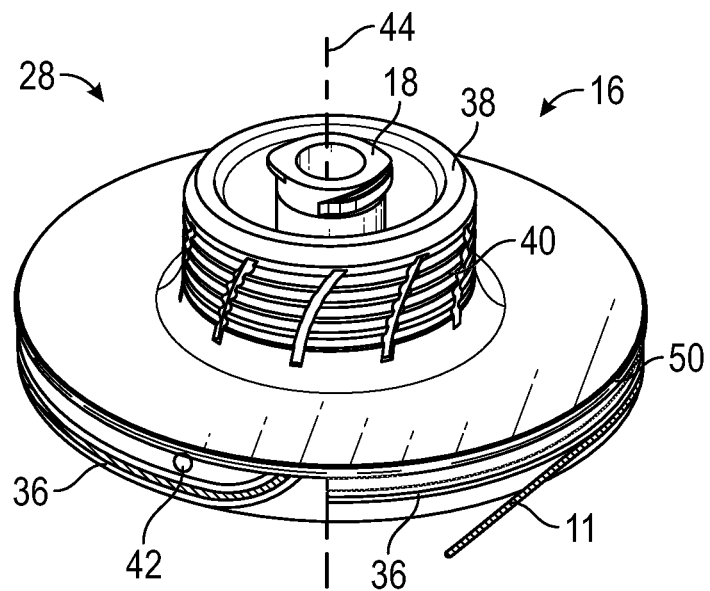
FIG. 1B is an example rotary element of the catheter system of FIG. 1A, according to some embodiments.

Referring now to FIG. 1B, in some embodiments, the rotary element 16 may include a support surface or groove 36, which may extend around at least a portion of a circumference of the rotary element 16. In some embodiments, the groove 36 may include a width approximately equal to or slightly greater than the instrument 11, which may facilitate support of the instrument 11 and/or decrease a risk of kinking of the instrument 11. In some embodiments, a length of the groove 36 may extend inwardly from the circumference of the rotary element 16, as illustrated in FIG. 1B, which may facilitate support of the instrument 11. In some embodiments, the instrument 11 may be disposed within the groove 36 and/or between the rotary element 16 and the housing 14. In some embodiments, a top surface of the rotary element 16 may include a protrusion 38, which may be proximate a user interface 40 configured for gripping by the user. FIG. 1B also illustrates an example O-ring 50, which will be explained later in further detail.

In some embodiments, the delivery device 10 may include a torque limiter, which may limit a torque of the user interface 40. In some embodiments, the torque limiter may limit the torque by slipping (as in, e.g., a friction plate slip-clutch, magnetic particle, or magnetic hysteresis torque limiter) or by uncoupling the load entirely (as in, e.g., a shear pin, synchronous magnetic, ball detent, or pawl and spring torque limiter). In further detail, in some embodiments, the user interface 40 may be coupled to and rotate with the rotary element 16 in response to the torque below a pre-determined, threshold value.

In some embodiments, the user may grip and turn the user interface 40 to advance and/or retract the instrument 11. In some embodiments, in response to the torque of the user interface 40 exceeding the threshold value, the user interface 40 may release from the rotary element 16 or slip with respect to the rotary element 16, which may prevent the instrument 11 from causing vascular damage, kinking, and/or buckling. In some embodiments, when the user interface 40 releases from the rotary element 16 or slips with respect to the rotary element 16, the user may not be able to rotate the rotary element 16 via the user interface 40. In some embodiments, the rotary element 16 may not include the torque limiter and/or the user interface 40. In these and other embodiments, the protrusion 38 may act as a grip for the user.

In some embodiments, rotation of the rotary element 16 with respect to the housing 14 may be accomplished via direct user input in which the user may physically interact with or touch the rotary element 16. For example, a hand of the user may take hold of the protrusion 38 and/or the user interface 40 to rotate the rotary element 16. In other embodiments, the rotation of the rotary element 16 with respect to the housing 14 may be driven through a mechanical coupling. In these and other embodiments, the user may not physically interact with or touch the rotary element 16 and/or the rotation of the rotary element 16 may occur in response to a linear or non-rotating action from the user. In some embodiments, the device may translate the linear or non-rotating action of the user into rotation of the rotary element 16. In some embodiments, the instrument 11 may be coupled with a power source through a rotationally allowable contact. In some embodiments, the housing 14 and/or the rotary element 16 may include a battery and/or power switch.

In some embodiments, the rotary element 16 may include a channel 42. In some embodiments, an outer opening of the channel 42 may be disposed above the instrument 11 and/or the groove 36, as illustrated, for example, in FIG. 1B. In some embodiments, the outer opening of the channel 42 may be disposed below the instrument 11 and/or the groove 36. In some embodiments, the outer opening of the channel 42 may be disposed within the groove 36. In some embodiments, the rotary element 16 may revolve or rotate around a central axis of rotation 44. In some embodiments, the outer opening of the channel 42 may be proximate the groove 36.

Figure 1C:
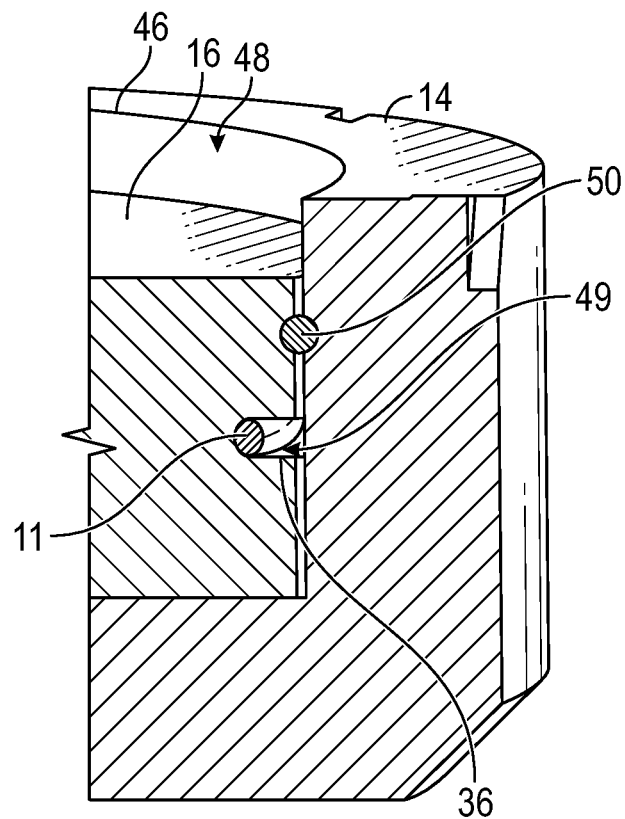
FIG. 1C is an enlarged partial cross-sectional view of an example delivery device of the catheter system of FIG. 1A, according to some embodiments.

Referring now to FIG. 1C, in some embodiments, the housing 14 may include a generally cylindrical inner surface 46, which may allow a generally cylindrical outer surface of the rotary element 16 to rotate with respect to the housing 14. In some embodiments, the housing 14 may include an inner surface that is another shape other than generally cylindrical, and an outer surface of the rotary element 16 may include a shape corresponding to the other shape that allows the rotary element 16 to rotate with respect to the housing 14. In some embodiments, the housing 14 may include an upper ledge (not illustrated) which may prevent the rotary element 16 from exiting an opening 48 of the housing 14. In some embodiments, the delivery device 10 may include one or more seals between the generally cylindrical inner surface 46 of the housing 14 and the generally cylindrical outer surface of the rotary element 16. In some embodiments, the seals may include one or more gaskets and/or one or more O-rings 50.

As illustrated in FIGS. 1B-1C, in some embodiments, a particular O-ring 50 may be annular, extending around the circumference of the rotary element 16 and between the rotary element 16 and the housing 14. In some embodiments, the particular O-ring 50 may isolate fluid pathways of the delivery device 10, including the channel 42 and a fluid pathway 49 that extends around the rotary element 16 in between the groove 36 and the housing 14 and out the port 15 around the instrument 11, from an external environment of the delivery device 10. In some embodiments, the fluid pathway 49 may be proximate and in fluid communication with the channel 42.

Figure 2A:
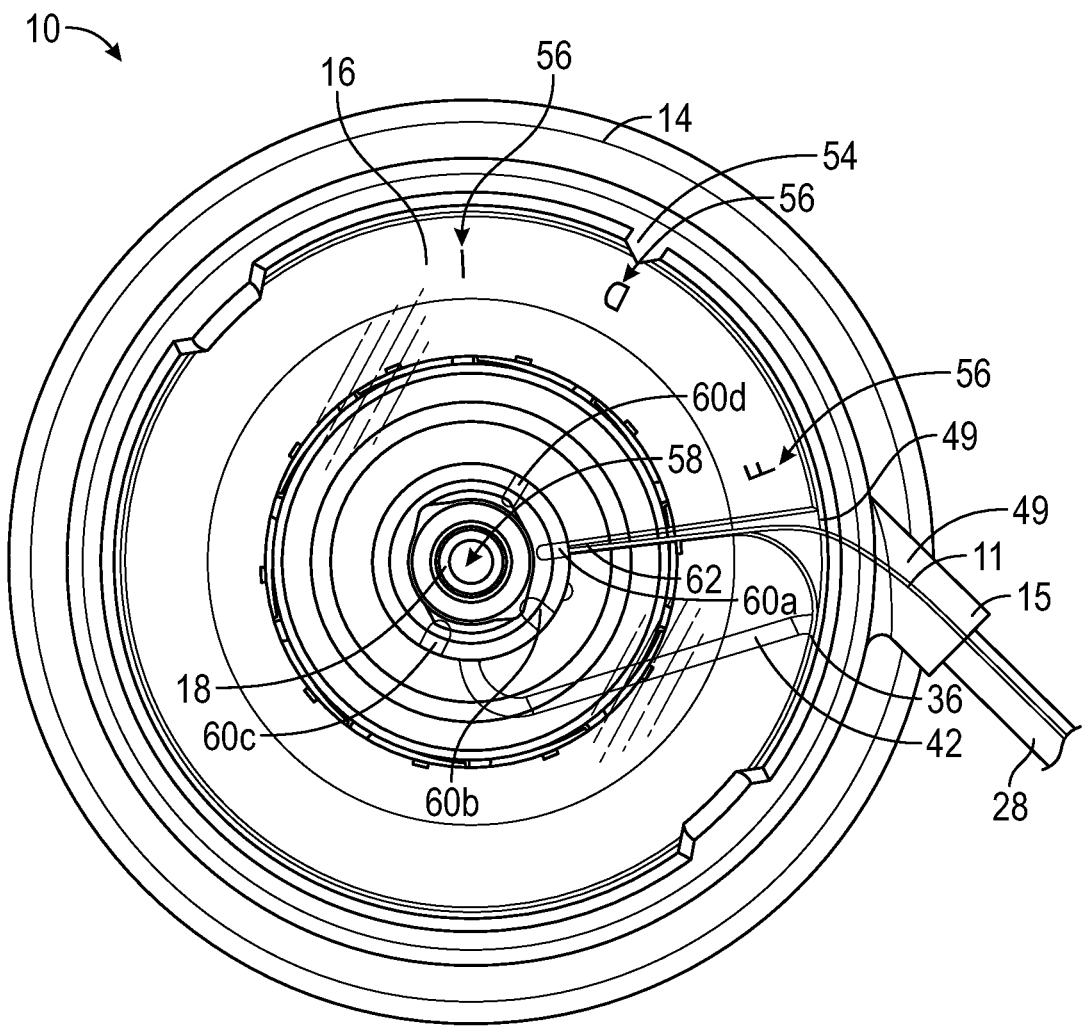
FIG. 2A is a top view of the delivery device of the catheter system of FIG. 1A, illustrating the rotary element in an example first position, according to some embodiments.
Figure 2B:
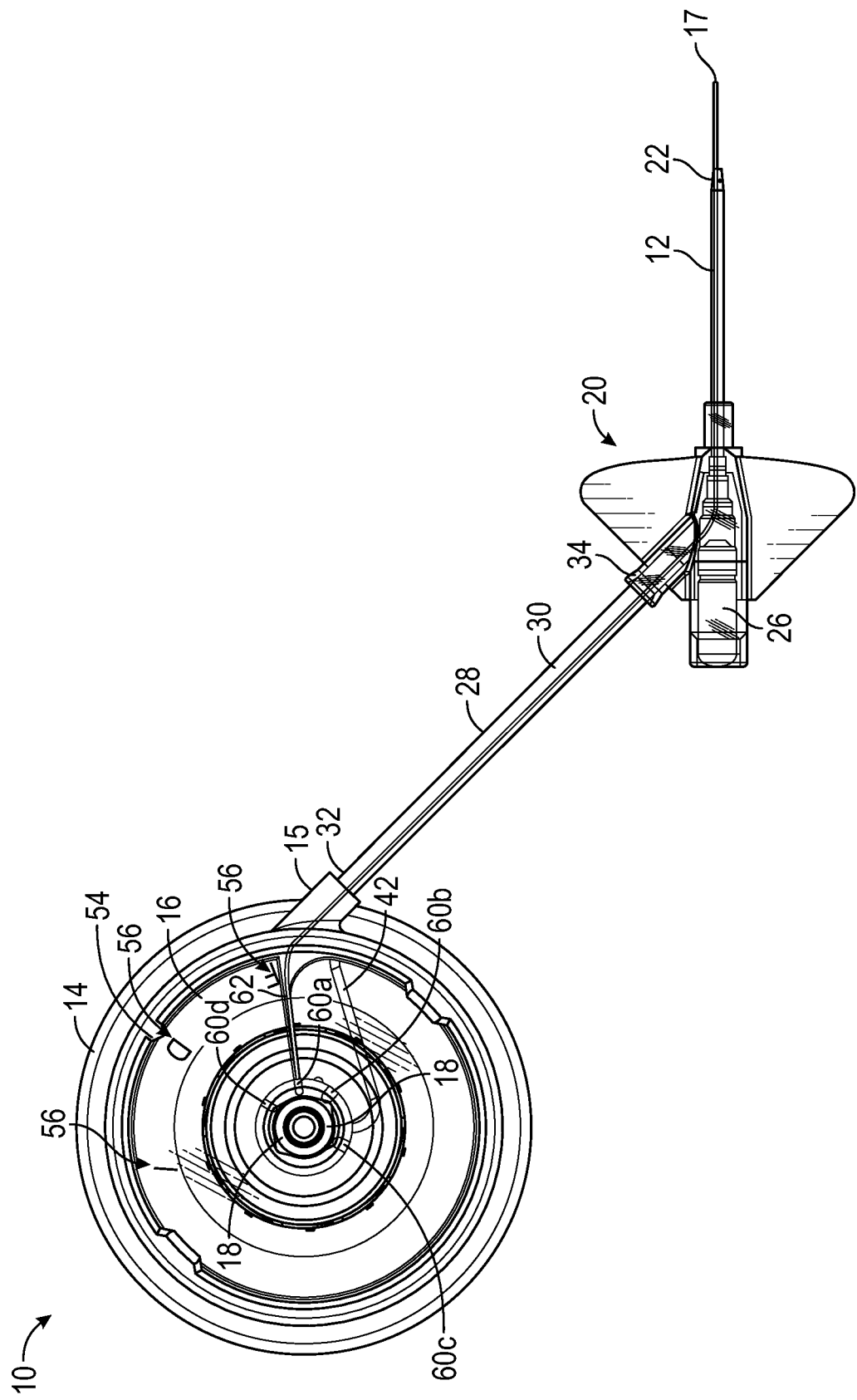
FIG. 2B is a top view of the catheter system of FIG. 1A, illustrating the rotary element in the first position, according to some embodiments.
Figure 2C:
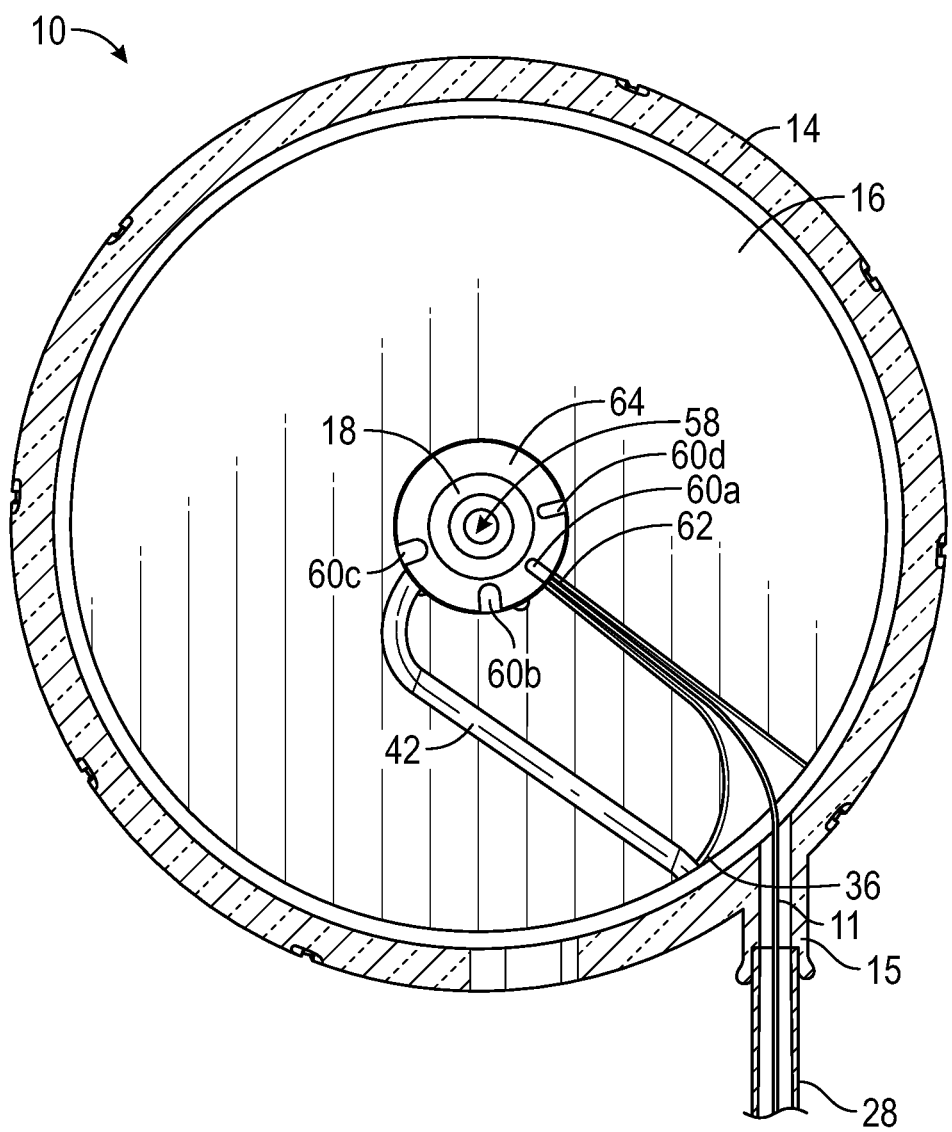
FIG. 2C is a cross-sectional view of the delivery device of the catheter system of FIG. 1A, illustrating the rotary element in the first position, according to some embodiments.

Referring now to FIGS. 2A-2C, the rotary element 16 is illustrated in a first position, according to some embodiments. In some embodiments, in response to the rotary element 16 being in the first position, a first end 17 of the instrument 11 may be disposed in a first location or position, which may be distal to the distal end 22 of the intravenous catheter 12 (illustrated, for example in FIG. 1A). In some embodiments, when the rotary element 16 is in the first position, the instrument 11 may extend directly out the port 15 without wrapping around the circumference of the rotary element 16. In other embodiments, when the rotary element 16 is in the first position, the instrument 11 may wrap around all or a portion of the circumference of the rotary element 16.

In some embodiments, the housing 14 may include a housing marker 54 which may be aligned with a rotary element marker 56 on the rotary element 16 when the rotary element 16 is in the first position. In some embodiments, the housing marker 54 and/or the rotary element marker 56 may include an indent, protrusion, character, etc. In some embodiments, the housing marker 54 and/or the rotary element marker 56 may include a detent that provides resistance to movement of the rotary element 16 from the detent. In some embodiments, when the rotary element 16 is in the first position, the housing marker 54 may be aligned with a particular rotary element marker 56, such as a "D" for "draw" or another an character, indent, detent, protrusion, color, etc.

In some embodiments, the connector 18 may include a primary fluid pathway 58 and multiple secondary fluid pathways 60 in fluid communication with the primary fluid pathway 58. In some embodiments, in response to the rotary element 16 being in the first position, a second end 62 of the instrument 11 may be aligned with the secondary fluid pathways 60, the channel 42 may not be aligned with the secondary fluid pathways 60, and the first end 17 of the instrument 11 may be disposed in the first location. As illustrated in FIG. 2A, for example, in response to the rotary element 16 being in the first position, the secondary fluid pathway 60a, with which the second end 62 of the instrument is aligned, may not be in fluid communication or may be fluidly isolated from the channel 42 and/or the fluid pathway 49. In some embodiments, a space between the groove 36 and an outer surface of the instrument 11 may be sealed such that fluid may not leak from the secondary fluid pathway 60a through the groove 36 around the instrument 11. In further detail, in some embodiments, a seal may be disposed around the second end 62 of the instrument 11 or within the housing 14 to fill the space and prevent fluid from contacting all or a portion of the groove 36 and travelling within the fluid pathway 49. In some embodiments, the seal may include an adhesive and/or potting agent.

In some embodiments, the first end 17 of the instrument 11 may be moveable, while the second end 62 of the instrument 11 may be secured. For example, the second end 62 of the instrument 11 may be secured within the groove 36 and/or proximate the secondary fluid pathway 60 when the rotary element 16 is in the first position. In some embodiments, a portion of the groove 36 disposed inwardly from the circumference may be part of a slit or tunnel. In some embodiments, the instrument 1 may be disposed within the groove 36 and supported on both sides of the instrument 11. In some embodiments, the groove 36 may extend towards the central axis of rotation 44 of the rotary element 16.

In some embodiments, the first position may correspond to a blood draw position, configured to collect blood from a patient. In some embodiments, when the rotary element 16 is in the first position, blood may be drawn from the patient through the instrument 11, into the secondary fluid pathway 60a, into the primary fluid pathway 58, and into the medical device 21, which may include a blood collection device. In some embodiments, blood may be prevented from travelling elsewhere within the delivery device 10, which may conserve a size of blood sample that is taken. In some embodiments, the blood collection device, such as, for example, a syringe, a vacuum tube, a blood collection tube, a holder, etc. may be coupled to the connector 18. In some embodiments, the instrument 11 may include tubing, which may facilitate collection of blood from the patient. In some embodiments, the tubing may include a variable inner diameter and/or a variable outer diameter.

Figure 3A:
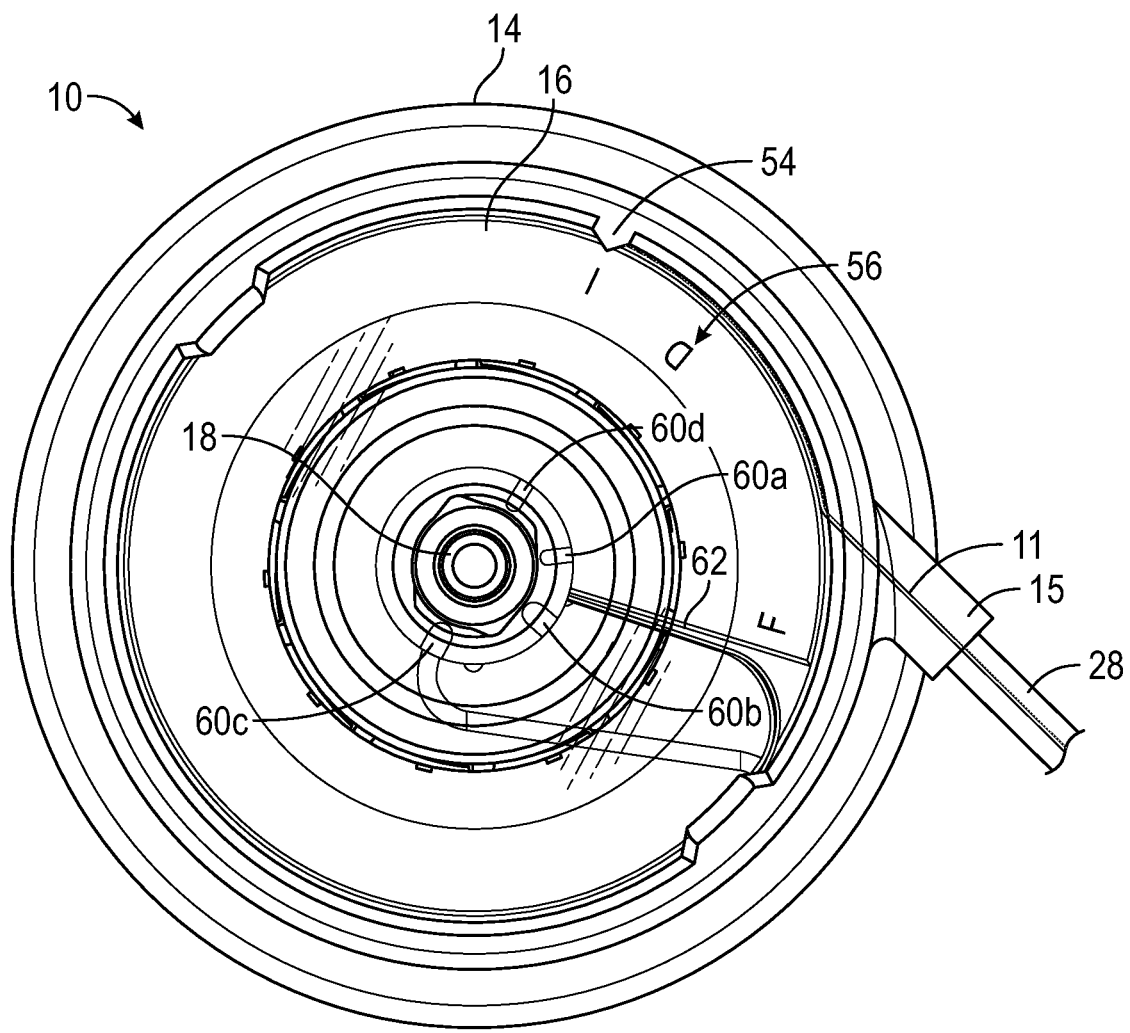
FIG. 3A is a top view of the delivery device of the catheter system of FIG. 1A, illustrating the rotary element in an example second position, according to some embodiments.
Figure 3B:
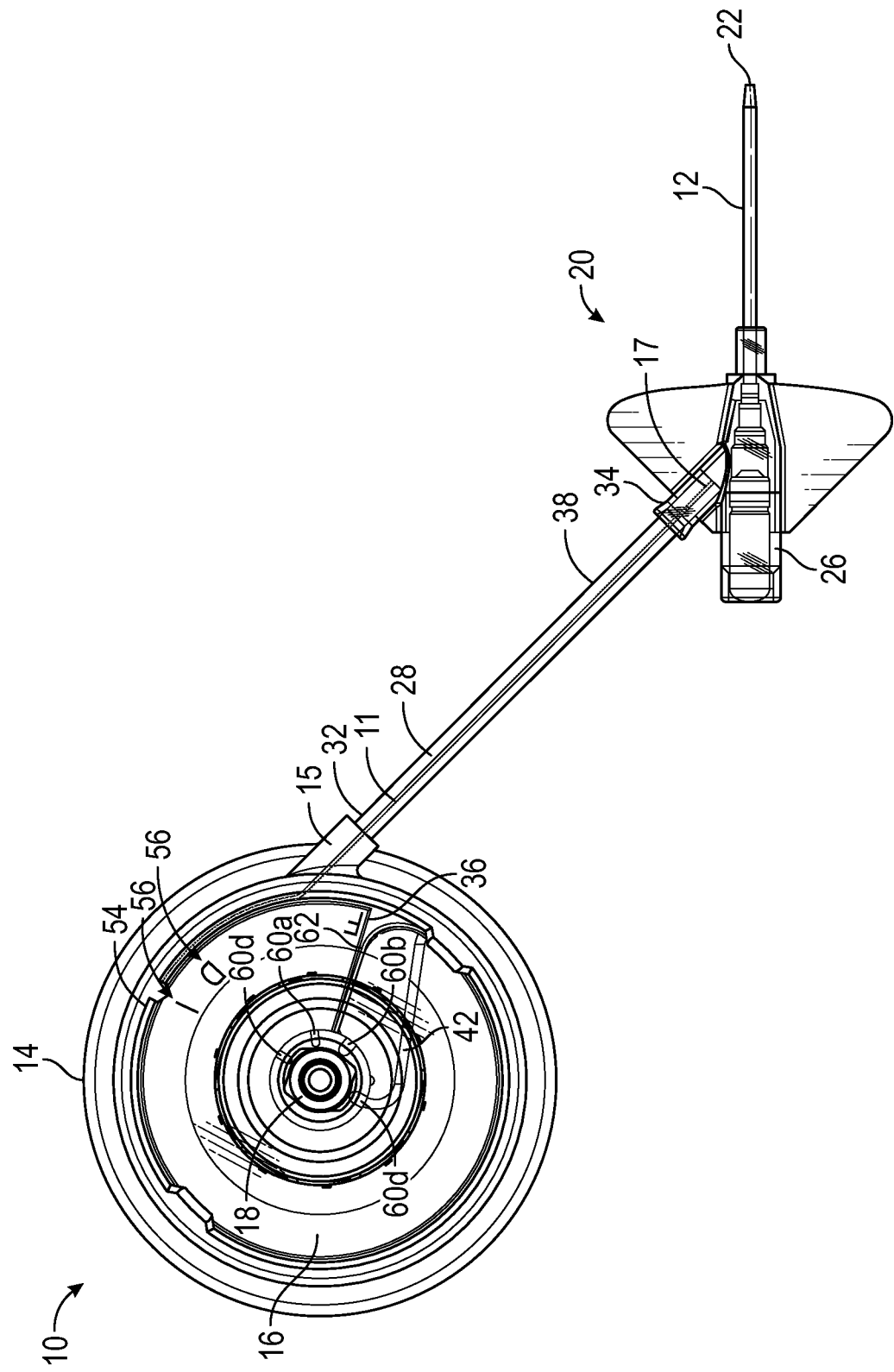
FIG. 3B is a top view of the catheter system of FIG. 1A, illustrating the rotary element in the second position, according to some embodiments.
Figure 3C:
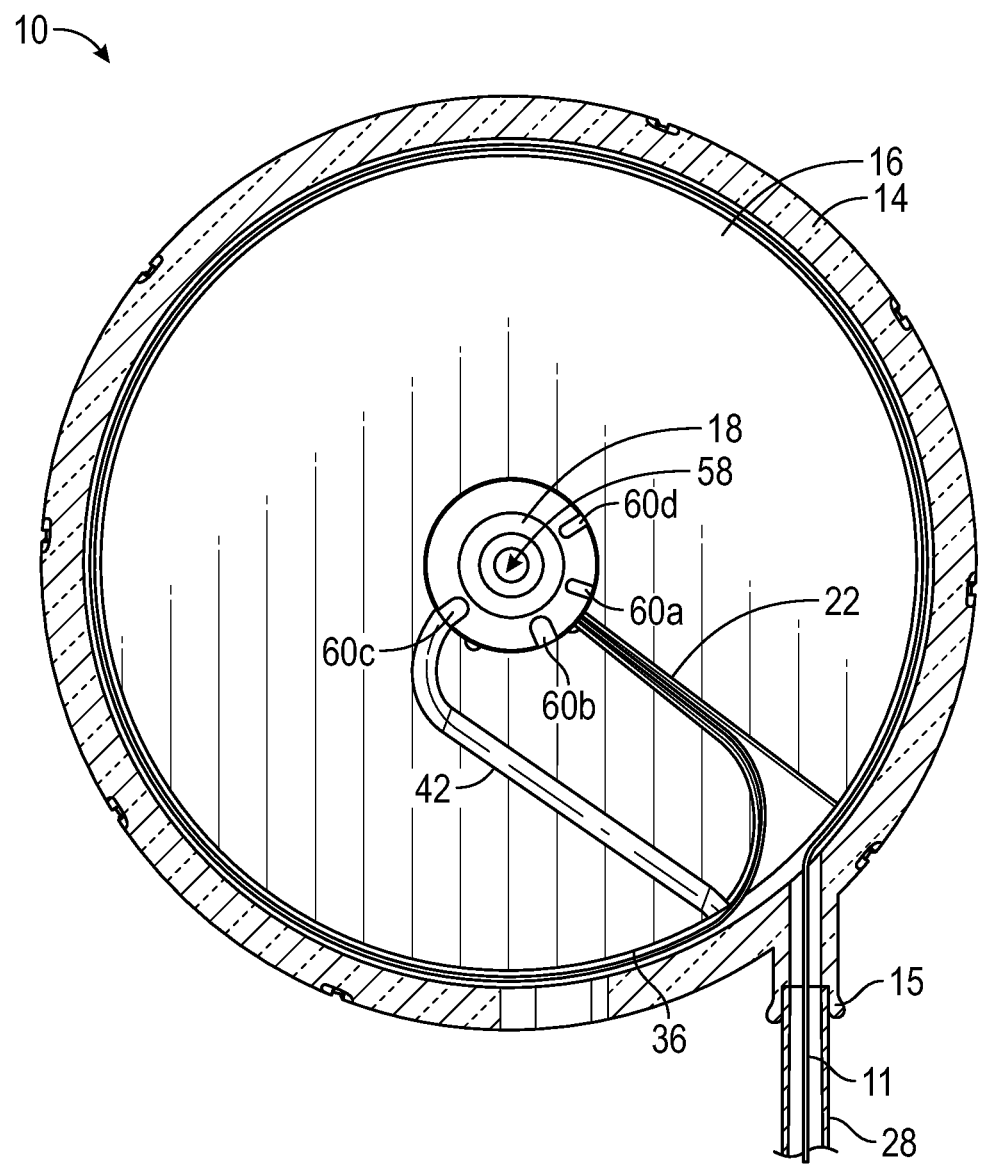
FIG. 3C is a cross-sectional view of the delivery device of the catheter system of FIG. 1A, illustrating the rotary element in the second position, according to some embodiments.

Referring now to FIGS. 3A-3C, the rotary element 16 is illustrated in a second position, according to some embodiments. In some embodiments, the second position may correspond to an infusion position, configured to infuse fluid into vasculature of the patient. In some embodiments, a fluid infusion device may be coupled to the connector 18. In some embodiments, the rotary element 16 may be configured to rotate with respect to the housing 14 between the first position and the second position.

In some embodiments, in response to the rotary element 16 being in the second position, the first end 17 of the instrument 11 may be disposed in a second location or position, which may be proximal to the distal end 22 of the intravenous catheter 12. In some embodiments, in response to the rotary element 16 being in the second position, the channel 42 may be aligned with the secondary fluid pathways 60, the second end 62 of the instrument 11 may not be aligned with the secondary fluid pathways 60, and the first end 17 of the instrument 11 may be disposed in the second location. In some embodiments, when the rotary element 16 is in the second position, the instrument 11 may wrap around all, a portion, or a substantial portion of the circumference of the rotary element 16.

In some embodiments, in response to the rotary element 16 being in the second position, fluid may be infused from the medical device 21 through the primary fluid pathway 58, through the secondary fluid pathway 60c, into the fluid pathway 49, through the extension tube 28, and through the catheter assembly 20. In some embodiments, in response to the rotary element 16 being in the second position, fluid may be prevented from flowing into the instrument 11, which may not be aligned with the secondary fluid pathways 60 and/or may be sealed from the secondary fluid pathways 60.

In some embodiments, in response to rotation of the rotary element 16 from the second position to the first position, the instrument 11 may be advanced distally through the port. In some embodiments, the rotary element 16 may rotate from the first position to the second position in response to rotation of the rotary element 16 less than a full turn or another amount. In some embodiments, the rotary element 16 may rotate from the first position to the second position in response to counter-clockwise rotation of the rotary element 16 less than the full turn or another amount. However, it is understood, that a configured of the delivery device 10 may be reversed, and in some embodiments, the rotary element 16 may rotate from the first position to the second position in response to clockwise rotation of the rotary element 16 less than the full turn or another amount. In some embodiments, when the rotary element 16 is in the second position, the housing marker 54 may be aligned with a particular rotary element marker 56, such as an "I" for "infuse" or another character, indent, detent, protrusion, etc.

Figure 4A:
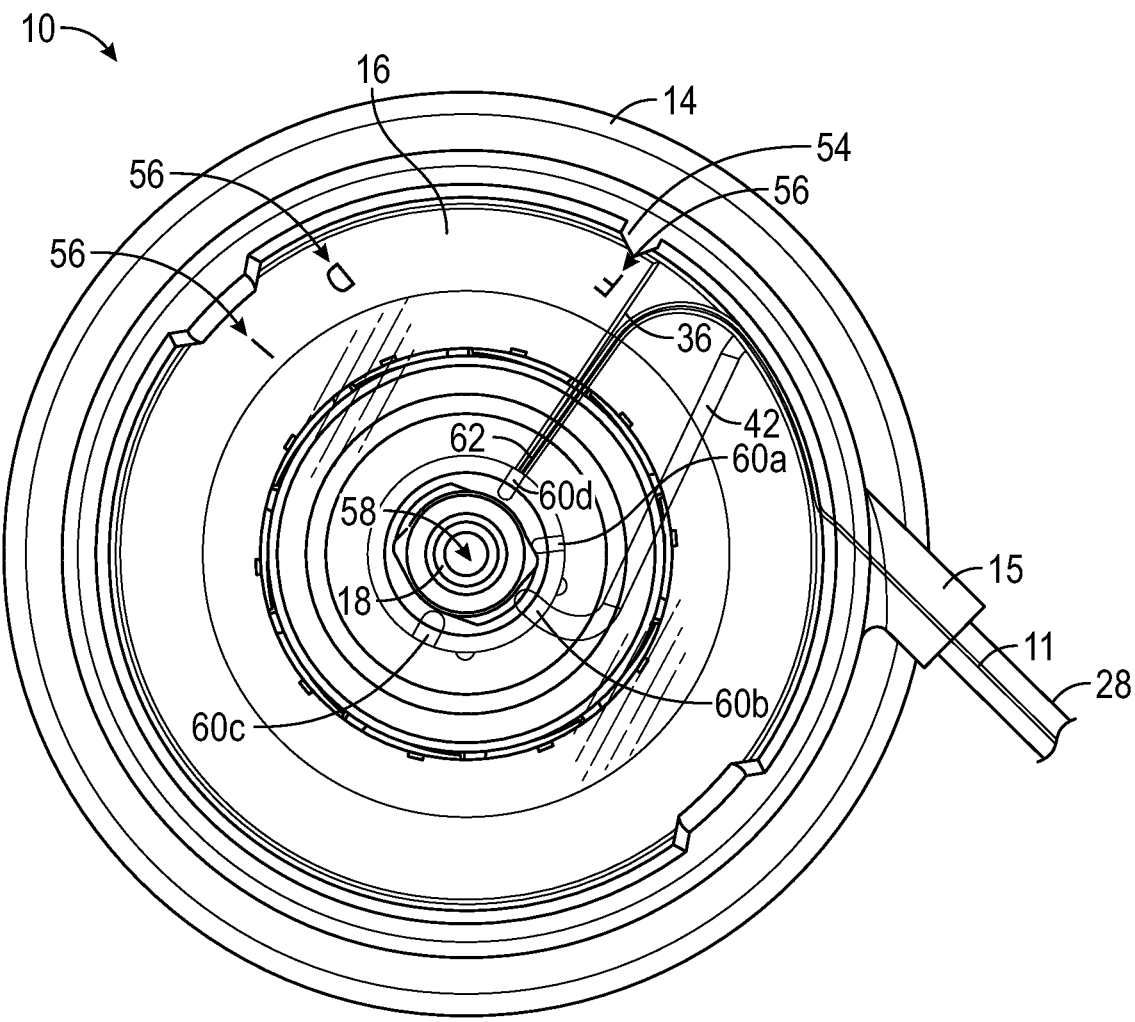
FIG. 4A is a top view of the delivery device of the catheter system of FIG. 1A, illustrating the rotary element in an example third position, according to some embodiments.
Figure 4B:
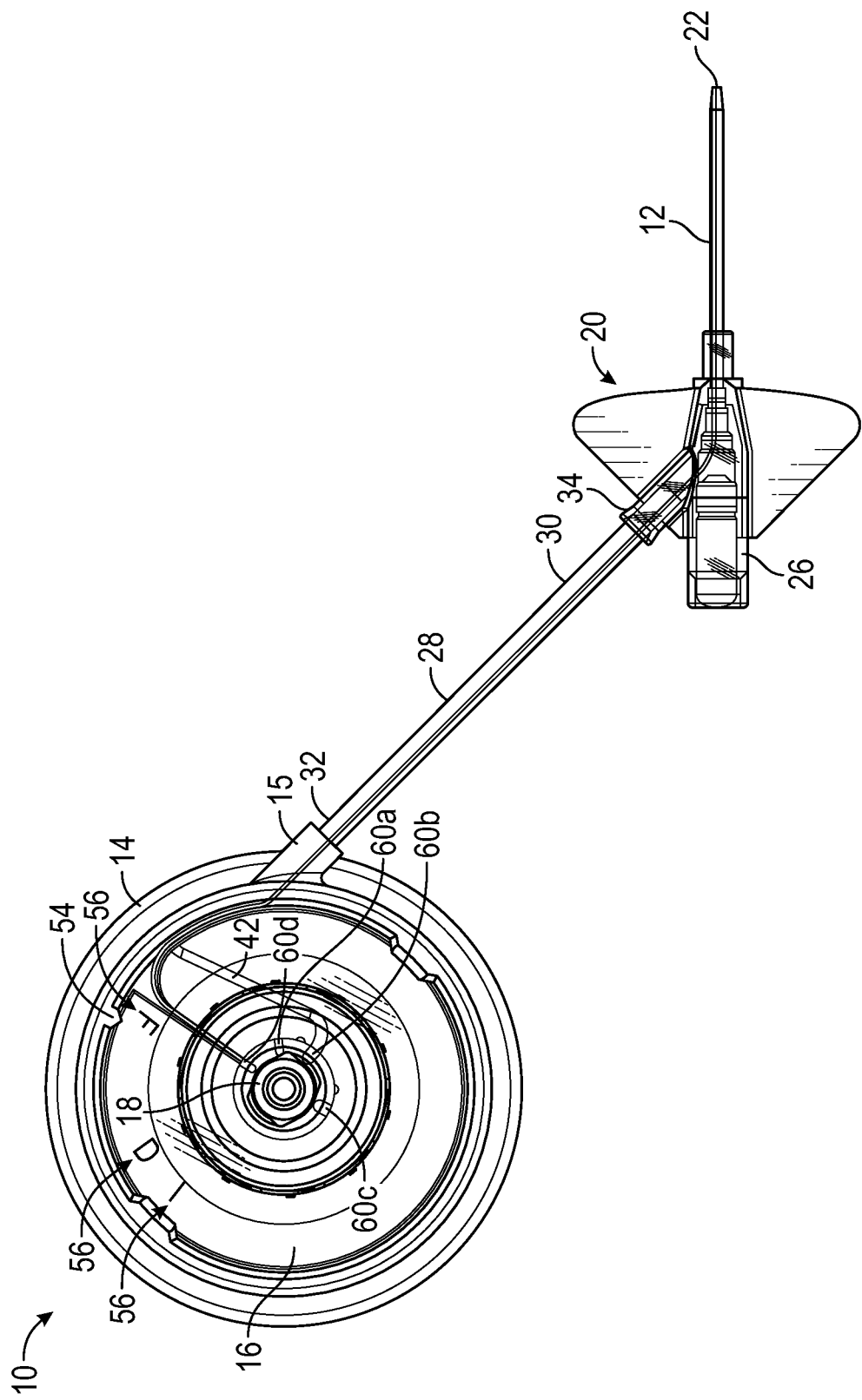
FIG. 4B is a top view of the catheter system of FIG. 1A, illustrating the rotary element in the third position, according to some embodiments.
Figure 4C:
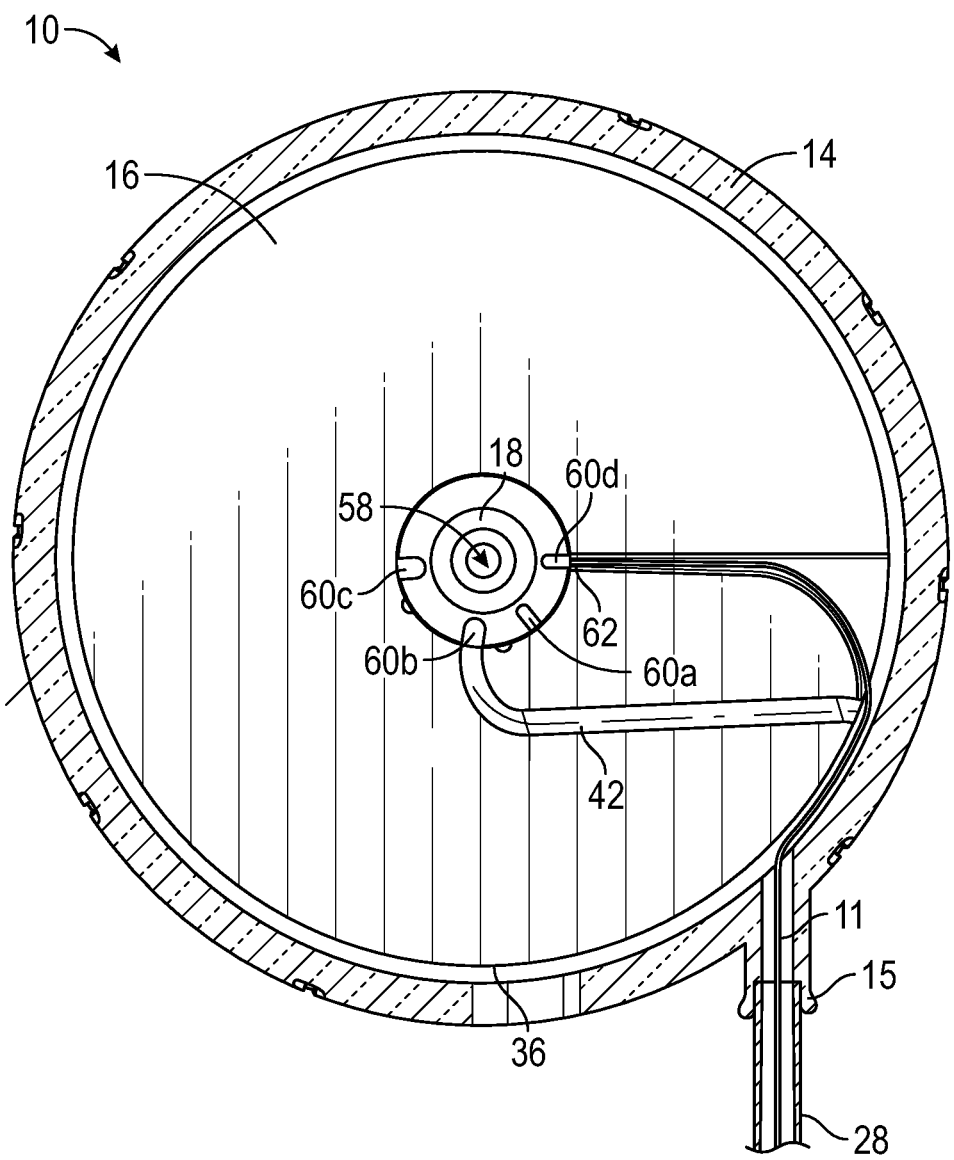
FIG. 4C is a cross-sectional view of the delivery device of the catheter system of FIG. 1A, illustrating the rotary element in the third position, according to some embodiments.

Referring now to FIGS. 4A-4C, in some embodiments, the rotary element 16 may be configured to rotate with respect to the housing 14 between the first position, the second position, and a third position. In some embodiments, the third position may correspond to a flush position, configured to flush the channel 42 and the instrument 11, which may include tubing. Thus, in some embodiments, the delivery device 10 may be configured to provide multiple functions, including blood draw, infusion, and flushing, via a single port, such as, for example, the port 15. In some embodiments, the groove 36 may be flushed when the rotary element 16 is in the third position.

In some embodiments, the instrument may include tubing, which may have properties and geometries that vary along the length of the tubing. In some embodiments, the properties and geometries of the tubing my vary to locally improve stiffness or compliance of the tubing, reduce a time to fill the blood collection device with blood, reduce a risk of sample degradation (hemolysis, etc.), or reduce vein trauma and associated downstream trauma.

In some embodiments, in response to the rotary element 16 being in the third position, the second end 62 of the instrument 11 may be aligned with the secondary fluid pathways 60, the channel 42 may be aligned with the secondary fluid pathways 60, and the first end 17 of the instrument 11 may be disposed in a third location or position, which may be proximal to the distal end 22 of the intravenous catheter 12 and/or distal to the second location. In some embodiments, when the rotary element 16 is in the third position, the instrument 11 may wrap around all, a portion, or a substantial portion of the circumference of the rotary element 16.

In some embodiments, in response to rotation of the rotary element 16 from the third position to the first position, the instrument 11 may be advanced distally through the port 15. In some embodiments, the rotary element 16 may rotate from the first position to the third position in response to rotation of the rotary element 16, counter-clockwise or clockwise, about one-fourth of a full turn or another amount. In some embodiments, when the rotary element 16 is in the third position, the housing marker 54 may be aligned with a particular rotary element marker 56, such as an "F" for "flush" or another an character, indent, detent, protrusion, etc.

In some embodiments, in response to the rotary element 16 being in the third position, fluid may be flushed from the medical device 21 through the primary fluid pathway 58, through the secondary fluid pathway 60b, into the fluid pathway 49, through the extension tube 28, and through the catheter assembly 20. In some embodiments, in response to the rotary element 16 being in the third position, fluid may also be flushed from the medical device 21 through the primary fluid pathway 58, through the secondary fluid pathway 60d, and through the instrument 11. In some embodiments, all fluid pathways within the delivery device 10 may be configured to be flushed in response to the rotary element 16 being in the third position.

In some embodiments, the rotary element 16 may be in a locked state in which the rotary element 16 is prevented from rotating with respect to the housing 14. In some embodiments, coupling of the medical device to the connector 18 and/or activation of a manual user input feature may unlock the rotary element 16, allowing rotation with respect to the housing 14. In some embodiments, the instrument 11 may be partially or fully retracted when the rotary element 16 is in the locked state. In some embodiments, the first end of the instrument 11 may be proximal to the second location when the rotary element 16 is in the locked state. In some embodiments, the delivery device 10 may include an automated passive feature that allows the rotary element 16 to rotate in response to coupling of the medical device 21 to the connector 18. In some embodiments, the instrument 11 may be prevented from prematurely exiting the delivery device 10 when the rotary element is in a "locked" state. In some embodiments, the delivery device 10 may include the manual user input feature, such as, for example, a lever or a button, that allows the rotary element 16 to rotate or prevents the rotary element 16 from rotating.

Although FIG. 1A illustrates a clamp on the extension tub 28, in some embodiments, the clamp may not be on the extension tube 28. In some embodiments, the rotary element 16 may be configured to rotate with respect to the housing 14 between the first position, the second position, the third position, and a fourth position. In some embodiments, the fourth position may correspond to a closed or sealed position, in which the channel 42 and the second end 62 of the instrument 11 are not aligned with and/or sealed from the secondary fluid pathways 60. In some embodiments, in response to the rotary element 16 being in the fourth position, one or more fluid pathways of the delivery device 10 may be sealed from an external environment of the delivery device 10.

In some embodiments, the fourth position may be disposed between the first position and the second position or between the second position and the third position. In some embodiments, rotary element 16 may be rotated clockwise or counter-clockwise from the first position, the second position, or the third position to reach the fourth position. In some embodiments, when the rotary element 16 is in the fourth position, the housing marker 54 may be aligned with a particular rotary element marker 56, such as a "C" for "closed" or another an character, indent, detent, protrusion, etc.

Figure 5A:
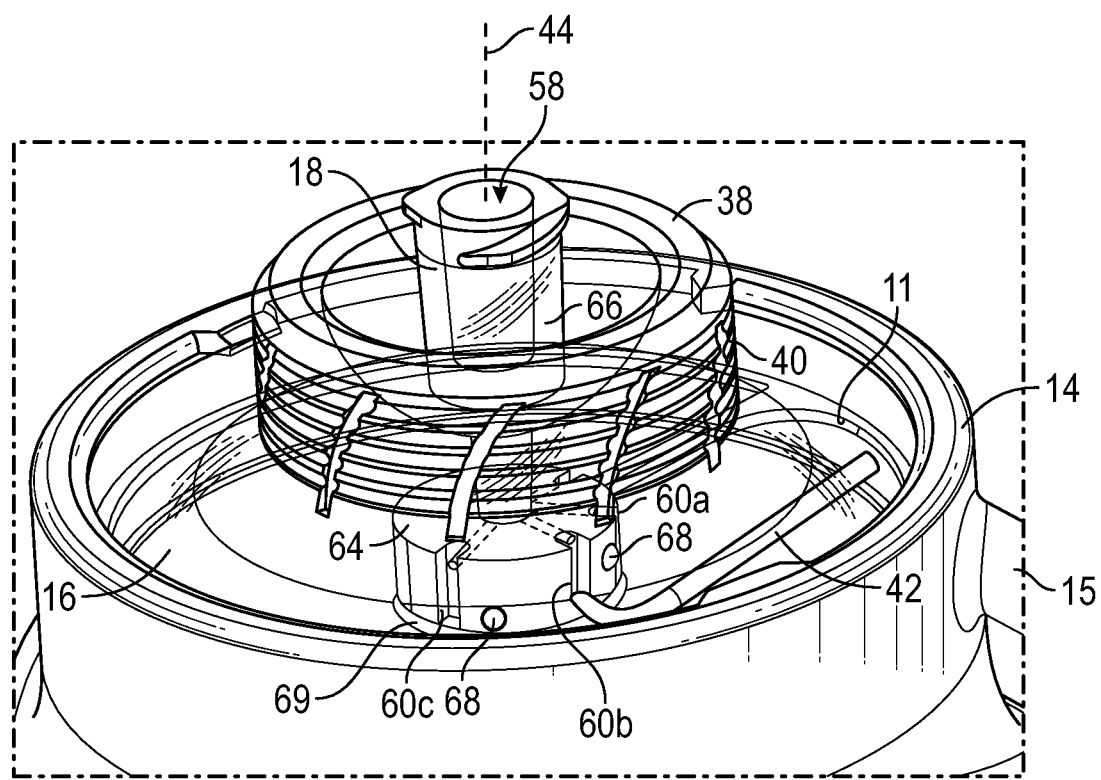
FIG. 5A is an upper perspective view of the delivery device of the catheter system of FIG. 1A, according to some embodiments.
Figure 5B:
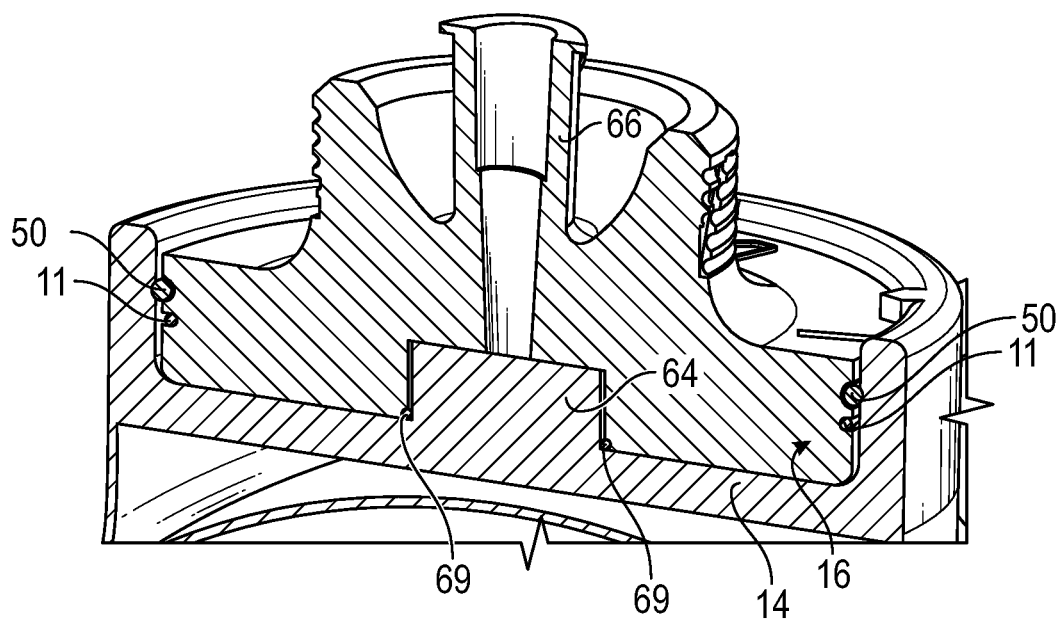
FIG. 5B is a cross sectional view of the delivery device of the catheter system of FIG. 1A, according to some embodiments.

Referring now to FIGS. 5A-5B, in some embodiments, connector 18 may include a base 64 and an upper portion 66 extending upwardly from the base 64. In some embodiments, the upper portion 66 of the base 64 may include a male or female luer adapter with a luer-slip or luer-lock feature, or another suitable adapter. In some embodiments, the base 64 may be fixed to the housing 14 and/or integrally formed with the housing 14 as a single unit. In some embodiments, the secondary fluid pathways 60 may extend along the base 64 and/or through the base 64 to connect to the primary fluid pathway 58.

In some embodiments, the base 64 may include one or more seals 68, which may be configured to align with the second end 62 of the instrument 11 and/or the groove 36 proximate the second end 62 of the instrument 11 when the rotary element 16 is disposed in one or more particular positions. For example, when the rotary element is in the first position, a particular seal 68 may be aligned with the channel 42 to seal the channel from the secondary fluid pathways 60, preventing blood from flowing into the channel 42 during blood collection, for example. As another example, when the rotary element is in the second position, a particular seal 68 may be aligned with the second end 62 of the instrument 11 to seal the instrument 11 from the secondary fluid pathways 60, preventing fluid from flowing through the instrument during infusion, for example. In some embodiments, the seals 68 may include protrusions configured to block fluid flow through the groove 36 and/or the second end 62 of the instrument 11.

In some embodiments, the rotary element 16 may rotate between one or more of the following: the first position, the second position, the third position, and the fourth position. In some embodiments, infusion may occur through the groove 36, and the rotary element 16 may not include channel 42. As illustrated in FIG. 5B, in some embodiments, another O-ring 69 may be disposed around the base 64. In some embodiments, the O-ring 69 may be annular, extending around a circumference of the base 64 and between the rotary element 16 and the housing 14. In some embodiments, the O-ring 69 may prevent fluid from leaking between the housing 14 and the rotary element 16.

Figure 6A:
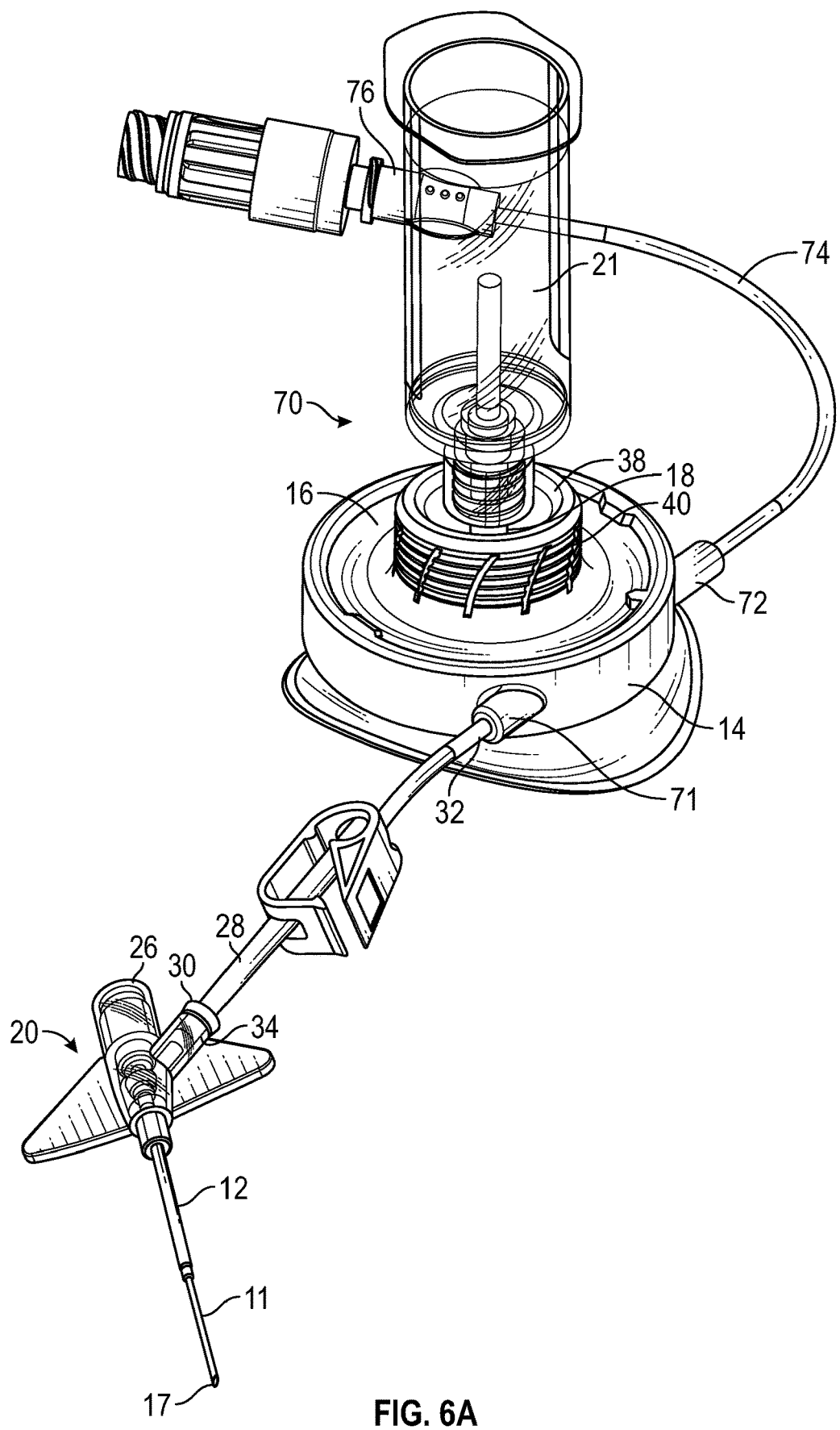
FIG. 6A is an upper perspective view of another catheter system, according to some embodiments.

Referring now to FIG. 6A, a delivery device 70 is illustrated, according to some embodiments. In some embodiments, the delivery device 70 may include or correspond to the delivery device 10. In some embodiments, the delivery device 70 may be similar, or identical, to the delivery device 10 disclosed in FIGS. 1-5 of the present disclosure in terms of one or more included components and/or operation. In some embodiments, the housing 14 may include a first port 71 and a second port 72.

In some embodiments, the second port 72 may be coupled to a distal end of another extension tube 74. In some embodiments, the distal end of the extension tube 74 may be integrated within the second port 72, which may eliminate manual connection of the delivery device to the other extension tube. In some embodiments, a proximal end of the other extension tube 74 may include a connector 76, which may be coupled to a medical device, such as an infusion device. In some embodiments, a blood collection device may be coupled to the connector 18 at a same time as the infusion device is coupled to the connector 76.

Figure 6B:
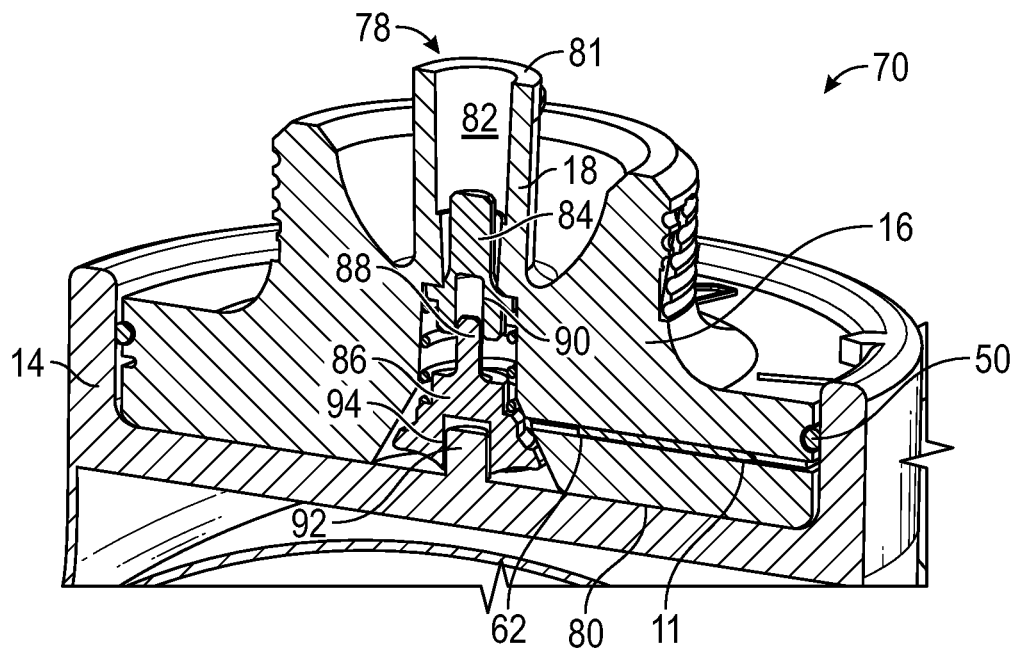
FIG. 6B is a cross-sectional view of an example delivery device of the catheter system of FIG. 6A.

Referring now to FIG. 6B, in some embodiments, the rotary element 16 may include an upper end 78 and a lower end 80. In some embodiments, the upper end 78 may include the connector 18 and an upper opening 81. In some embodiments, the rotary element 16 may include a lumen 82, which may extend through the upper end 78 and the lower end 80. In some embodiments, the rotary element 16 may include an upper septum 84 and/or a lower septum 86 disposed within the lumen 82.

In some embodiments, the lower septum 86 may be disposed in a portion of the lumen 82 that is tapered and a bottom of the lower septum 86 may be wider than a top of the lower septum 86, which may prevent unwanted upward movement of the lower septum 86. In some embodiments, the top of the lower septum 86 may include a protrusion 88 configured to fit within a groove 90 of the upper septum 84. In some embodiments, a protrusion 92 of the lower housing 14 may be disposed within a groove 94 of a bottom of the lower septum 86, which may facilitate centering of the lower septum 86 within the lumen 82.

Figure 6C:
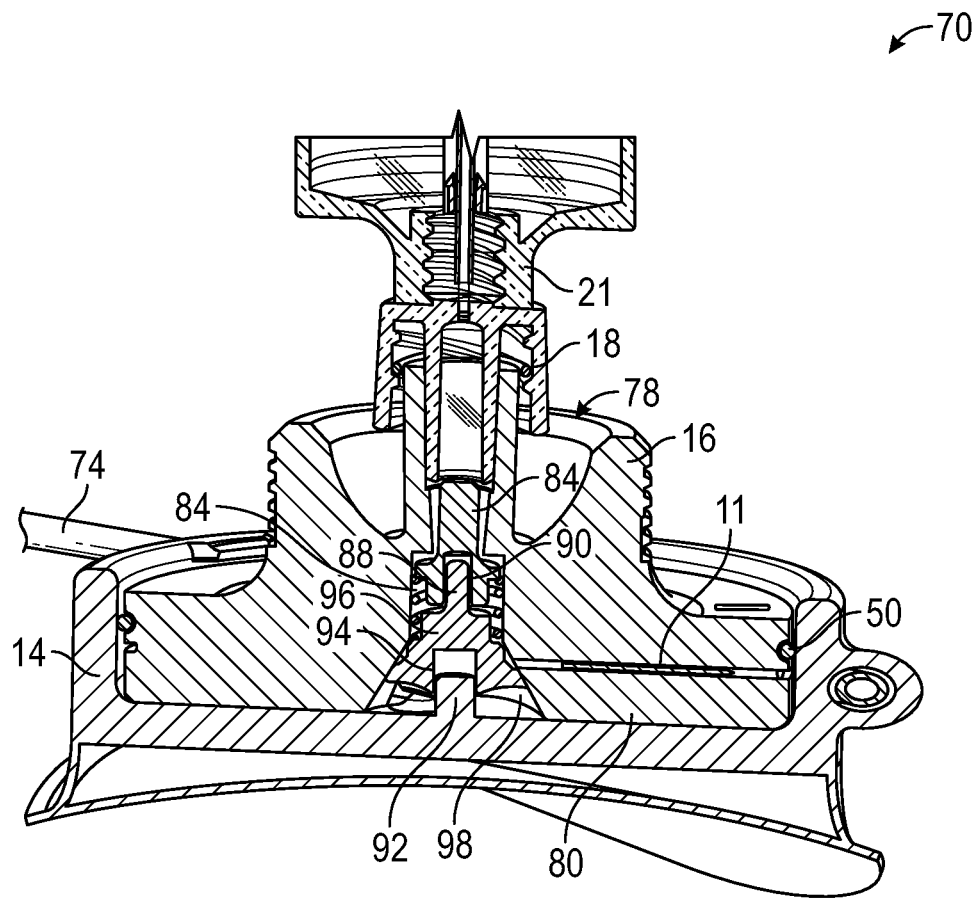
FIG. 6C is a cross-sectional view of the delivery device of the catheter system of FIG. 6A, illustrating an example medical device coupled to an example connector of the delivery device and an example rotary element in an example first position.

Referring now to FIG. 6C, in some embodiments, in response to connection of the medical device 21 to the connector 18, the upper septum 84 may be configured to move towards the lower septum 86 to allow fluid to flow around the upper septum 84.

Figure 6D:
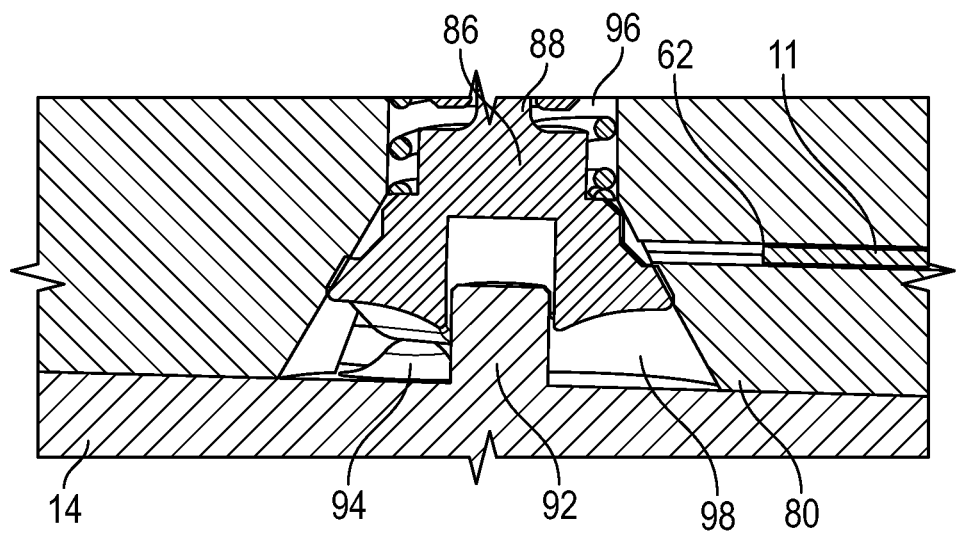
FIG. 6D is an enlarged cross-sectional view of the delivery device of the catheter system of FIG. 6A, illustrating the rotary element in the first position, according to some embodiments.

Referring now to FIGS. 6C-6D, in some embodiments, the housing 14 may include a protrusion 94. in some embodiments, in response to the rotary element 16 being rotated to a first position: the lower septum 86 may contact the protrusion 94 and be moved towards the upper opening 81; the lower septum 86 may divide the lumen 82 into an upper chamber 96 and a lower chamber 98 sealed from the upper chamber 96; the upper chamber 96 may be in fluid communication with the second end 62 of the instrument 11; the instrument 11 may extends through the first port 71; and the first end 17 of the instrument 11 may be disposed in a particular first location. In some embodiments, the second port 72 may be in fluid communication with the lower chamber 98.

In some embodiments, the upper chamber 96 may be in fluid communication with the upper opening 81 when the upper septum 84 is moved toward the lower septum 86. In some embodiments, the upper chamber 96 may not be in fluid communication with the upper opening 81 when the upper septum 84 when the medical device 21 is removed from the connector 18. In some embodiments, the upper chamber 96 may be disposed between a lower surface of the upper septum 84 and an upper surface of the lower septum 86. In some embodiments, the lower chamber 98 may be disposed between a lower surface of the lower septum 86 and the housing 14.

Figure 7A:
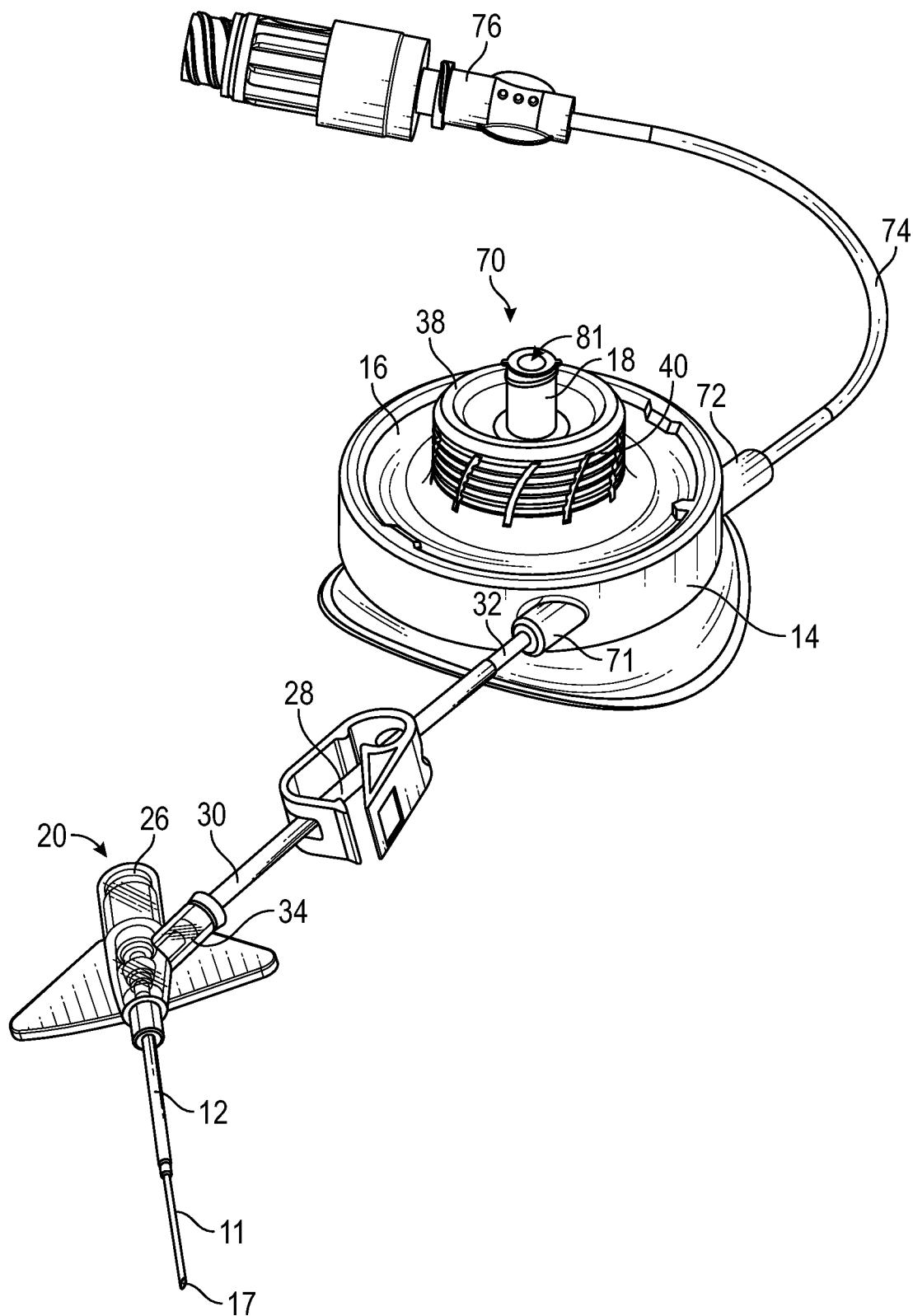
FIG. 7A is an upper perspective view of the catheter system of FIG. 6A, illustrating the rotary element in an example second position, according to some embodiments.
Figure 7B:
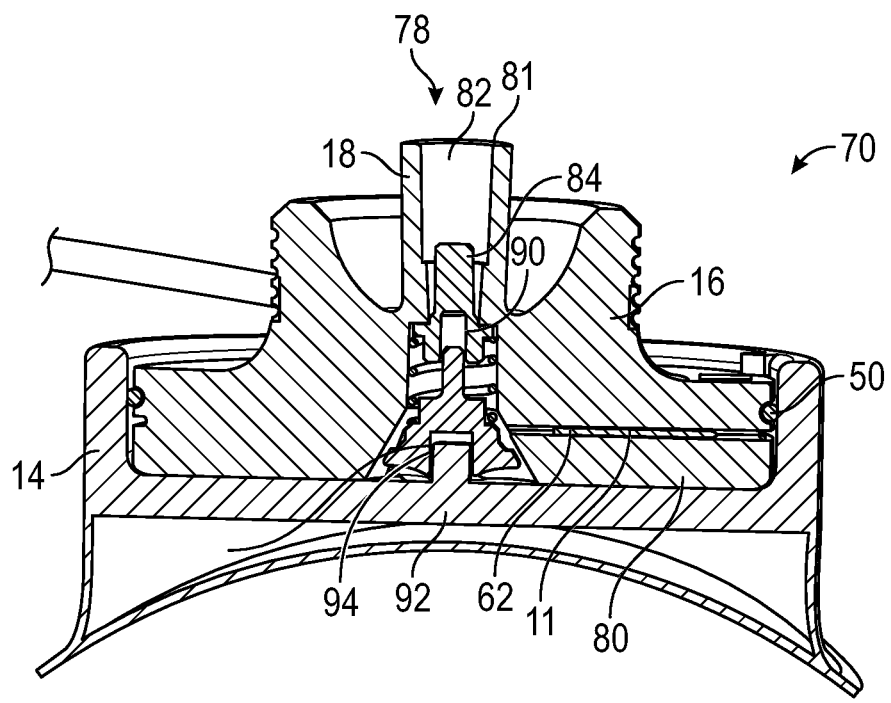
FIG. 7B is a cross-sectional view of the delivery device of the catheter system of FIG. 6A, illustrating the rotary element in the second position.
Figure 7C:
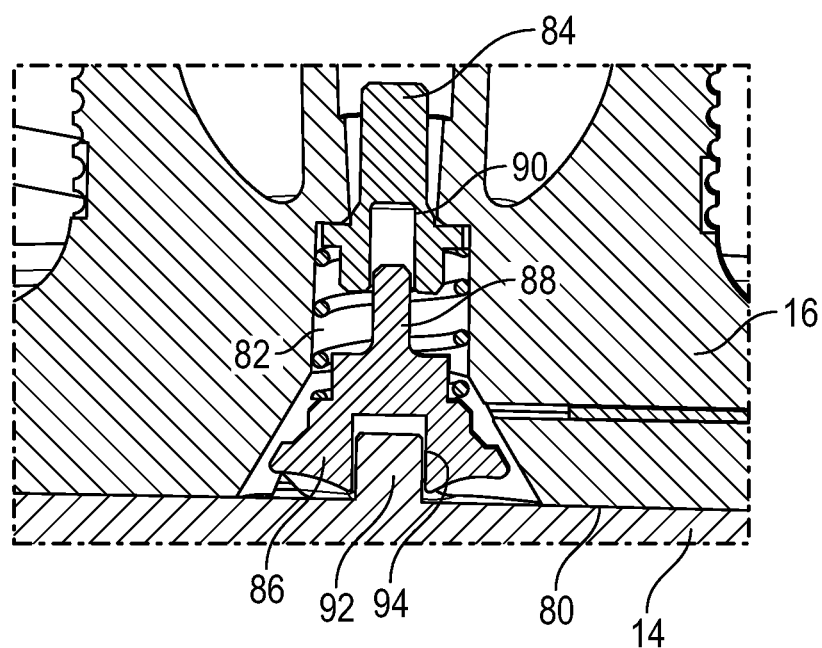
FIG. 7C is an enlarged cross-sectional view of the delivery device of the catheter system of FIG. 7B, illustrating the rotary element in the second position, according to some embodiments.

Referring now to FIGS. 7A-7C, in some embodiments, in response to the rotary element 16 being rotated to a second position, the lower septum 86 may move away from the upper opening 81; the upper chamber 96, the lower chamber 98, and the second end 62 of the instrument 11 may be in fluid communication; and the first end 17 of the instrument 11 may be disposed in a particular second location. In some embodiments, the lumen 82 may include a spring 100, which may urge the upper septum 84 upwardly against the housing 14 to prevent fluid from flowing around the upper septum 84.

Figure 8A:
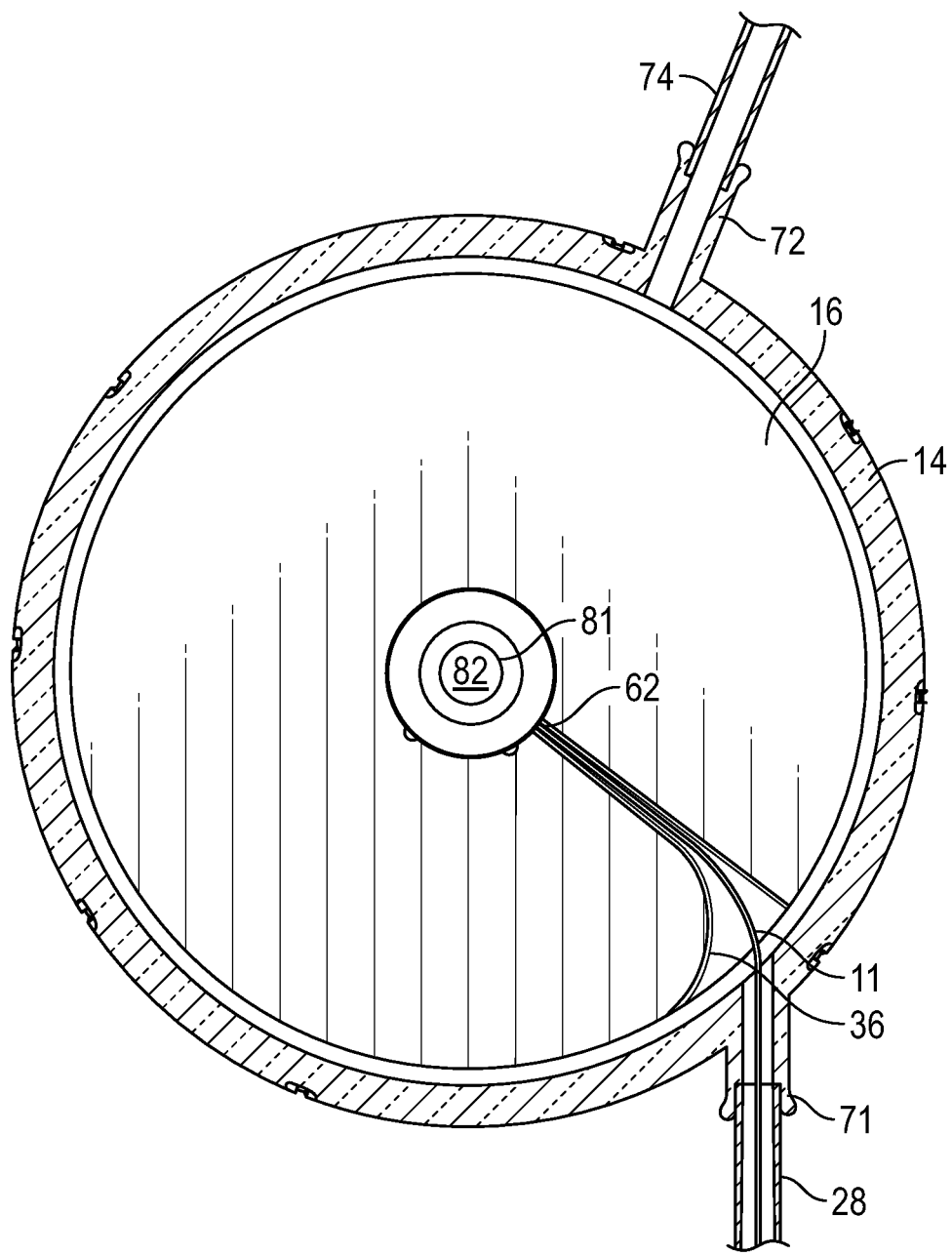
FIG. 8A is a cross-sectional view of the delivery device of the catheter system of FIG. 6A, illustrating the rotary element in the first position.
Figure 8B:
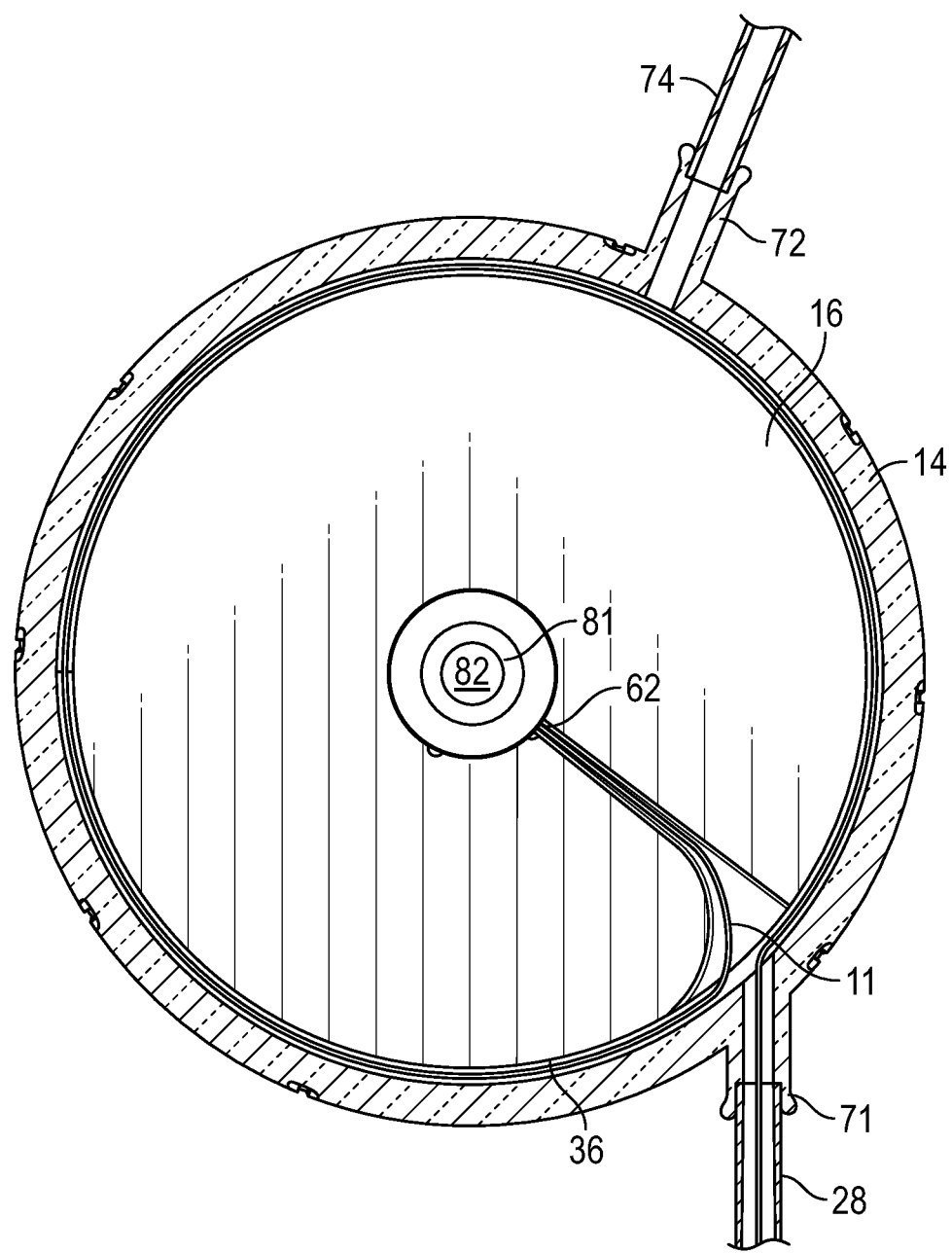
FIG. 8B is a cross-sectional view of the delivery device of the catheter system of FIG. 6A, illustrating the rotary element in the second position.
Figure 8C:
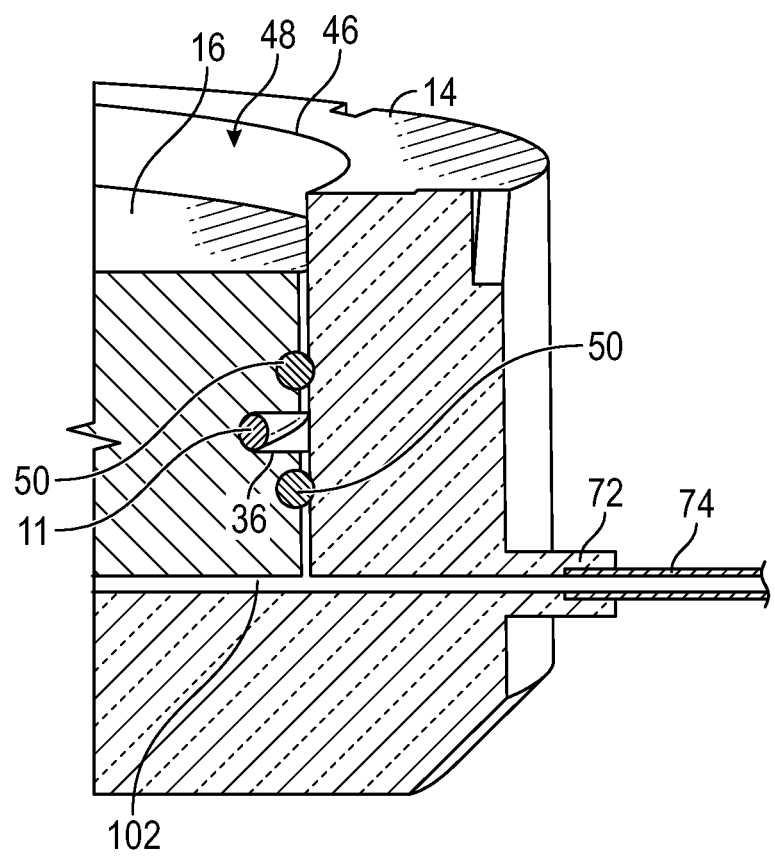
FIG. 8C is an enlarged partial cross-sectional view of the delivery device of the catheter system of FIG. 6A, according to some embodiments.

Although FIGS. 6A and 7A illustrate a clamp on the extension tub 28, in some embodiments, the clamp may not be on the extension tube 28. In some embodiments, the rotary element 16 may be configured to rotate with respect to the housing 14 between another position, which may correspond to a closed or sealed position. In some embodiments, when the rotary element 16 is in the closed position, one or more fluid pathways of the delivery device 10 may be sealed from an external environment of the delivery device 10. As an example, when the rotary element 16 is in the closed position, the upper septum 84 and/or the lower septum 86 may seal the channel 102 and/or the second port 72 and prevent fluid communication between the second port 72 and the lower chamber 98, Referring now to FIG. 8A, the rotary element 16 is illustrated in the first position, according to some embodiments. Referring now to FIG. 8B, the rotary element 16 is illustrated in the second position, according to some embodiments. Referring now to FIG. 8C, in some embodiments, the delivery device 70 may include one or more seals between the generally cylindrical inner surface 46 of the housing 14 and the generally cylindrical outer surface of the rotary element 16. In some embodiments, the seals may include a gasket and/or an O-ring 50.

In some embodiments, the delivery device 70 may include a channel 102 disposed between the lower end 80 of the rotary element 16 and the housing 14. In some embodiments, the channel 102 may be in fluid communication with the second port 72 and the lower chamber 98 when the rotary element 16 is in the first position and/or the second position.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A delivery device for delivering an instrument through an intravenous catheter, comprising:
 a housing, comprising a port;
 a connector, wherein the connector comprises:
  a primary fluid pathway; and
  a plurality of secondary fluid pathways in fluid communication with the primary fluid pathway;

a rotary element disposed within the housing and coupled to the connector, wherein the connector extends through the rotary element, wherein the rotary element comprises:
  a groove extending around at least a portion of a circumference of the rotary element; and
  a channel; and
the instrument, comprising a first end and a second end, wherein the instrument is disposed within the groove and between the rotary element and the housing,
wherein the rotary element is configured to rotate with respect to the housing between a first position and a second position,
wherein in response to the rotary element being in the first position, the second end of the instrument is aligned with the plurality of secondary fluid pathways, the channel is not aligned with the plurality of secondary fluid pathways, and the first end of the instrument is disposed in a first location;
wherein in response to the rotary element being in the second position, the channel is aligned with the plurality of secondary fluid pathways, the second end of the instrument is not aligned with the plurality of secondary fluid pathways, and the first end of the instrument is disposed in a second location.

2. The delivery device of claim 1, wherein in response to rotation of the rotary element from the second position to the first position, the instrument is advanced distally through the port.

3. The delivery device of claim 1, wherein the rotary element rotates from the first position to the second position in response to rotation of the rotary element less than a full turn.

4. The delivery device of claim 1, wherein the rotary element is configured to rotate with respect to the housing between the first position, the second position, and a third position, wherein in response to the rotary element being in the third position, the second end of the instrument is aligned with the plurality of secondary fluid pathways, the channel is aligned with the plurality of secondary fluid pathways, and the first end of the instrument is disposed in a third location.

5. The delivery device of claim 4, wherein in response to rotation of the rotary element from the third position to the first position, the instrument is advanced distally through the port.

6. The delivery device of claim 4, wherein the rotary element rotates from the first position to the third position in response to rotation of the rotary element about one-fourth of a full turn.

7. The delivery device of claim 1, wherein the instrument comprises tubing.

8. The delivery device of claim 1, wherein the connector comprises a luer adapter.

9. The delivery device of claim 1, further comprising an extension tube integrated within the port.

10. The delivery device of claim 1, wherein the second end of the instrument is secured within the groove.

11. The delivery device of claim 1, wherein the groove extends inwardly from the circumference toward a central axis of rotation of the rotary element.

12. A catheter system, comprising:
  a catheter assembly, comprising:
    a catheter adapter; and
    a catheter having a distal end, wherein the catheter extends distally from the catheter adapter; and
  a delivery device coupled to the catheter assembly, comprising:
    a housing, comprising a port;
    a connector, wherein the connector comprises:
      a primary fluid pathway; and
      a plurality of secondary fluid pathways in fluid communication with the primary fluid pathway;
    a rotary element disposed within the housing and coupled to the connector, wherein the connector extends through the rotary element, wherein the rotary element comprises:
      a groove extending around at least a portion of a circumference of the rotary element; and
      a channel; and
    an instrument, comprising a first end and a second end, wherein the instrument is disposed within the groove and between the rotary element and the housing,
    wherein the rotary element is configured to rotate with respect to the housing between a first position and a second position,
    wherein in response to the rotary element being in the first position, the second end of the instrument is aligned with the plurality of secondary fluid pathways, the channel is not aligned with the plurality of secondary fluid pathways, and the first end of the instrument is disposed in a first location, wherein the first location is distal to the distal end of the catheter,
    wherein in response to the rotary element being in the second position, the channel is aligned with the plurality of secondary fluid pathways, the second end of the instrument is not aligned with the plurality of secondary fluid pathways, and the first end of the instrument is disposed in a second location, wherein the second location is proximal to the distal end of the catheter.

13. The catheter system of claim 12, further comprising an extension tube, comprising a proximal end and a distal end, wherein the proximal end of the extension tube is integrated within the port, wherein the distal end of the extension tube is integrated within the catheter adapter.

14. The catheter system of claim 12, wherein the instrument comprises tubing.

15. A delivery device for delivering an instrument through an intravenous catheter, comprising:
  a housing, comprising a first port, a second port, and a protrusion;
  a rotary element disposed within the housing, wherein the rotary element comprises:
    a groove extending around at least a portion of a circumference of the rotary element;
    an upper end, comprising a connector;
    a lower end;
    a lumen extending through the upper end and the lower end;
    an upper septum disposed within the lumen;
    a lower septum disposed within the lumen, wherein in response to connection of a medical device to the connector, the upper septum is configured to move towards the lower septum to allow fluid to flow around the upper septum, and
  the instrument, comprising a first end and a second end, wherein the instrument is disposed within the groove and between the rotary element and the housing,
  wherein the rotary element is configured to rotate with respect to the housing between a first position and a second position,
  wherein in response to the rotary element being rotated to the first position, the lower septum contacts the protrusion and is moved towards an opening, the lower septum divides the lumen into an upper chamber and a lower chamber sealed from the upper chamber, the upper chamber is in fluid communication with the second end of the instrument, the instrument extends through the first port, and the first end of the instrument is disposed in a first location, wherein the second port is in fluid communication with the lower chamber;

wherein in response to the rotary element being rotated to the second position, the lower septum moves away from the opening, the upper chamber, the lower chamber, and the second end of the instrument are in fluid communication, and the first end of the instrument is disposed in a second location.

16. The delivery device of claim 15, further comprising a spring disposed within the lumen, wherein the spring urges the upper septum upwardly against the housing to prevent the fluid from flowing around the upper septum.

17. The delivery device of claim 15, wherein the instrument comprises tubing.

18. The delivery device of claim 15, wherein the second end of the instrument is secured within the groove.

19. The delivery device of claim 15, further comprising a channel disposed between the lower end of the rotary element and the housing, wherein the channel is in fluid communication with the lower chamber.

20. The delivery device of claim 15, wherein the connector comprises a luer adapter.

* * * * *